(12) United States Patent
Djupesland

(10) Patent No.: US 7,841,337 B2
(45) Date of Patent: Nov. 30, 2010

(54) BREATH-ACTUATED NASAL DELIVERY DEVICE

(75) Inventor: Per Gisle Djupesland, Oslo (NO)

(73) Assignee: Optinose AS, Oslo (NO)

( * ) Notice: Subject to any disclaimer, the term of this patent is extended or adjusted under 35 U.S.C. 154(b) by 523 days.

(21) Appl. No.: 10/489,187

(22) PCT Filed: Sep. 6, 2002

(86) PCT No.: PCT/IB02/03849

§ 371 (c)(1),
(2), (4) Date: Sep. 28, 2004

(87) PCT Pub. No.: WO03/020350

PCT Pub. Date: Mar. 13, 2003

(65) Prior Publication Data

US 2005/0028812 A1  Feb. 10, 2005

Related U.S. Application Data

(63) Continuation-in-part of application No. 09/700,532, filed on Nov. 15, 2000, now Pat. No. 6,715,485.

(30) Foreign Application Priority Data

Sep. 6, 2001 (GB) .................................. 0121568.0
Jun. 12, 2002 (WO) ....................... PCT/IB02/03034

(51) Int. Cl.
*A61M 11/02* (2006.01)
*A61M 11/08* (2006.01)
*A61M 15/08* (2006.01)
*B65D 83/06* (2006.01)

(52) U.S. Cl. ........................... 128/200.23; 128/203.15; 128/203.18; 128/203.22

(58) Field of Classification Search ............ 128/203.15, 128/200.14, 200.23, 200.24, 201.23, 201.28, 128/203.18, 203.22, 203.29
See application file for complete search history.

(56) References Cited

U.S. PATENT DOCUMENTS 5,046,493 A  9/1991  Kropkowski et al.

(Continued)

FOREIGN PATENT DOCUMENTS

DE  3018691  11/1981

(Continued)

OTHER PUBLICATIONS

U.S. Appl. No. 11/567,286, filed Dec. 6, 2006, Djupesland.

(Continued)

*Primary Examiner*—Danton DeMille
(74) *Attorney, Agent, or Firm*—Proskauer Rose LLP; Kristin Neuman, Esq.; Issac A. Hubner, Esq.

(57) ABSTRACT

A breath-actuated nasal delivery device, comprising: a mouthpiece through which a user in use exhales to actuate the delivery device; a nosepiece for fitting to a nostril of the user through which a substance is in use delivered; a substance supply unit actuatable to deliver a dose of a substance through the nosepiece; a loading unit operable to load the substance supply unit with an actuation force; and a release mechanism for enabling actuation of the substance supply unit in response to exhalation by the user through the mouthpiece; wherein the release mechanism comprises a locking unit which is movable: between a locking configuration in which the substance supply unit is locked in a non-actuated position when loaded by the loading unit and a release configuration in which the substance supply unit is actuatable by the loading unit, and a trigger member for releasing the locking unit from the locking configuration to the release configuration in response to exhalation by the user through the mouthpiece and thereby enabling actuation of the substance supply unit.

39 Claims, 20 Drawing Sheets

U.S. PATENT DOCUMENTS

| | | | |
|---|---|---|---|
| 5,060,643 | A | 10/1991 | Rich et al. |
| 5,069,204 | A | 12/1991 | Smith et al. |
| 5,355,873 | A | 10/1994 | Del Bon et al. |
| 5,373,841 | A | 12/1994 | Kyllonen et al. |
| 6,470,882 | B1 | 10/2002 | Newhouse et al. |
| 6,715,485 | B1 * | 4/2004 | Djupesland ............ 128/203.15 |
| 6,948,495 | B2 * | 9/2005 | Seppala ................. 128/203.15 |
| 7,347,201 | B2 | 3/2008 | Djupesland |
| 7,377,901 | B2 | 5/2008 | Djupesland et al. |
| 7,481,218 | B2 | 1/2009 | Djupesland |
| 2004/0112378 | A1 | 6/2004 | Djupesland |
| 2004/0112379 | A1 | 6/2004 | Djupesland |
| 2004/0149289 | A1 * | 8/2004 | Djupesland ............ 128/207.18 |
| 2004/0182388 | A1 | 9/2004 | Djupesland |
| 2005/0072430 | A1 | 4/2005 | Djupesland |
| 2005/0235992 | A1 | 10/2005 | Djupesland |
| 2006/0096589 | A1 | 5/2006 | Djupesland |
| 2006/0169278 | A1 | 8/2006 | Djupesland |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2007/0186927 | A1 | 8/2007 | Djupesland et al. |
| 2008/0161771 | A1 | 7/2008 | Djupesland |
| 2008/0163874 | A1 | 7/2008 | Djupesland |
| 2008/0221471 | A1 | 9/2008 | Djupesland |
| 2008/0223363 | A1 | 9/2008 | Djupesland |
| 2008/0289629 | A1 | 11/2008 | Djupesland |

FOREIGN PATENT DOCUMENTS

| | | |
|---|---|---|
| EP | 0 414 536 | 2/1991 |
| GB | 408856 | 4/1934 |
| GB | 2 349 092 | 10/2000 |
| GB | 2 374 537 | 10/2002 |
| GB | 2 374 807 | 10/2002 |
| GB | 2 378 393 | 2/2003 |
| SE | 8102793-0 | 12/1983 |
| WO | 90/01963 | 3/1990 |
| WO | 98/53869 | 12/1998 |
| WO | 99/49916 | 10/1999 |
| WO | 00/16835 | 3/2000 |
| WO | 00/51672 | 9/2000 |

OTHER PUBLICATIONS

U.S. Appl. No. 11/816,984, filed Aug. 23, 2007, Djupesland.
U.S. Appl. No. 12/161,466, filed Jul. 18, 2008, Djupesland.
U.S. Appl. No. 12/279,285, filed Aug. 13, 2008, Djupesland.
U.S. Appl. No. 12/279,291, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/339,716, filed Dec. 19, 2008, Djupesland.
U.S. Appl. No. 12/375,115, filed Jan. 26, 2009, Djupesland.

* cited by examiner

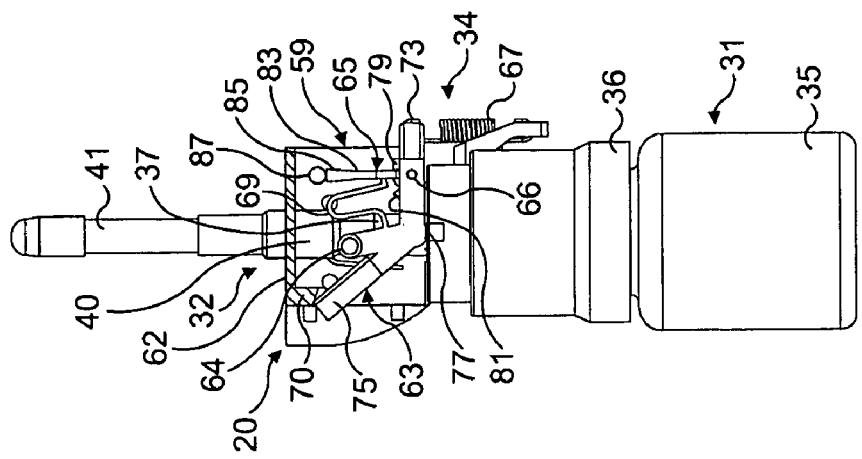
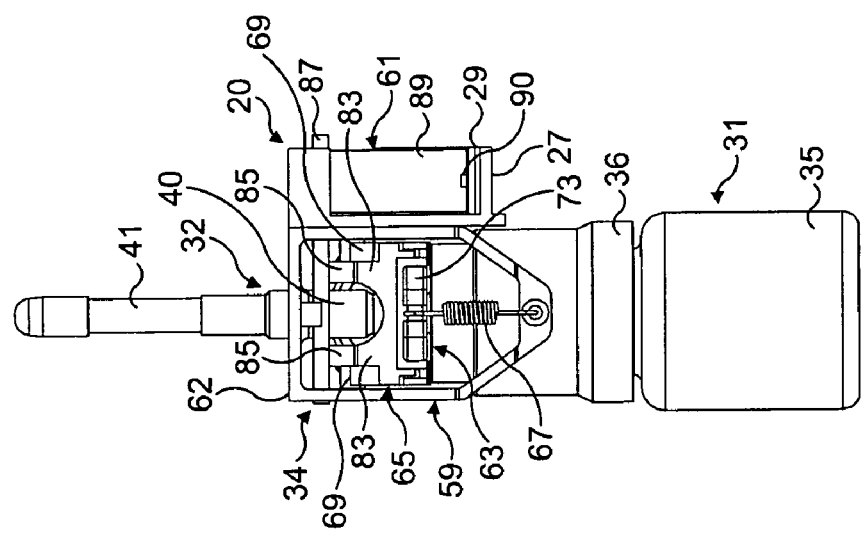
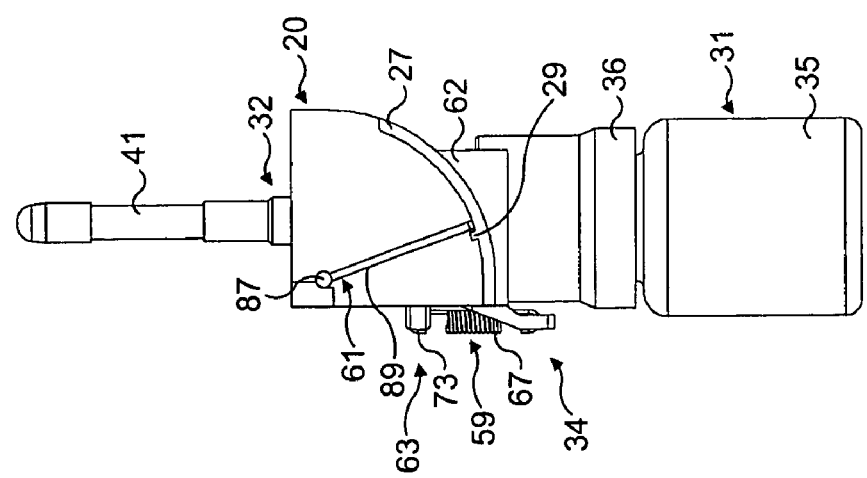

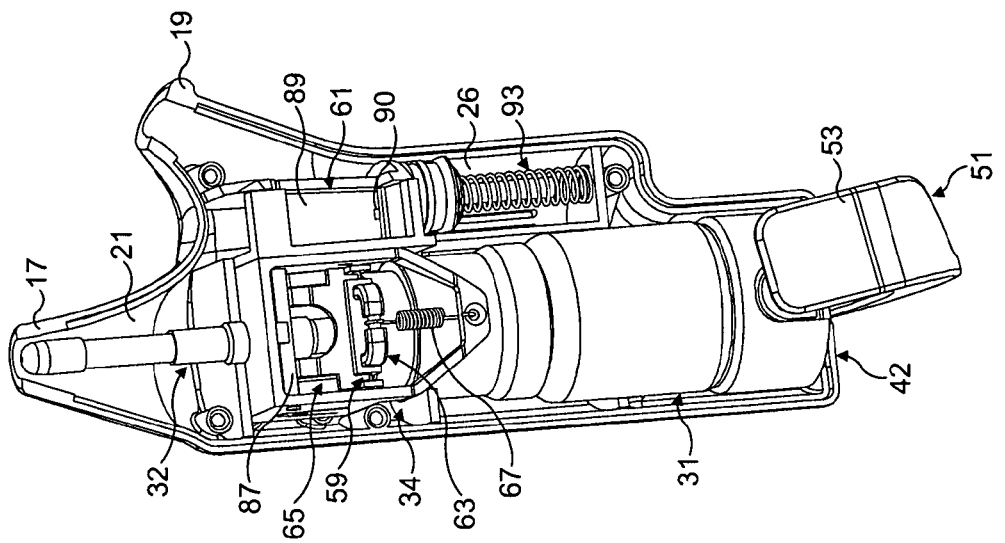
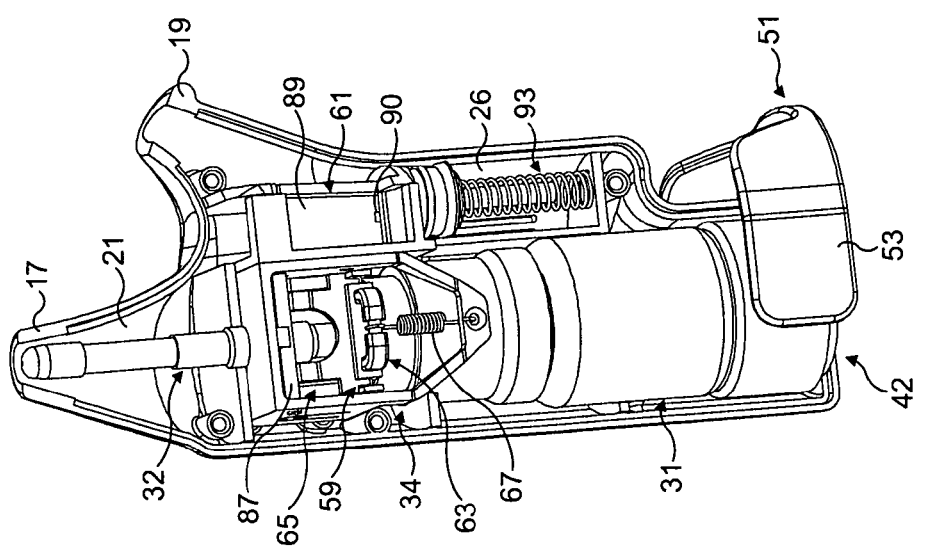

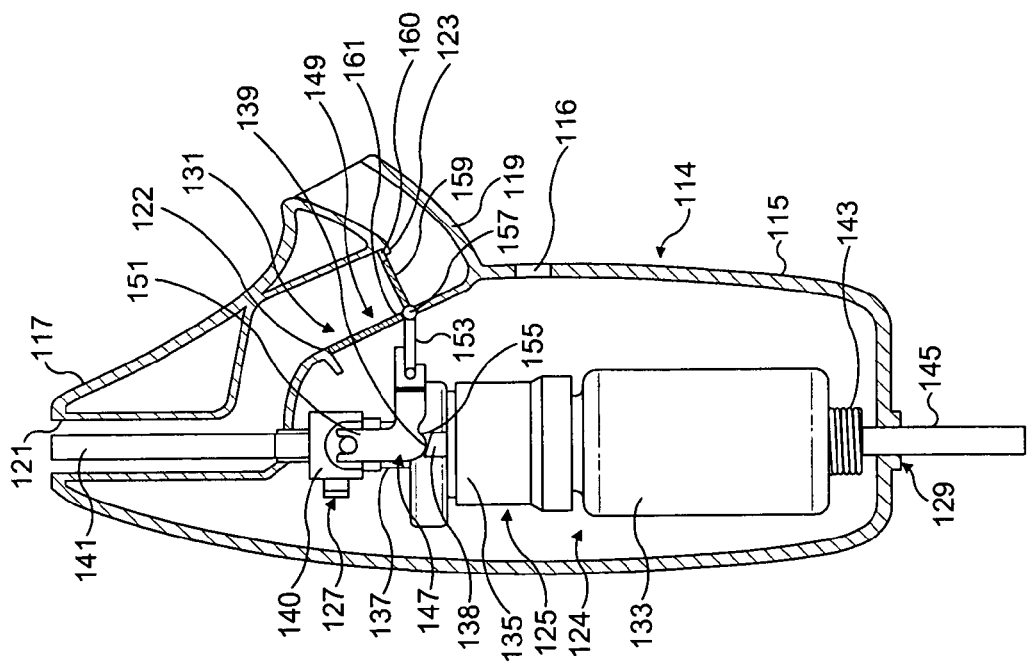
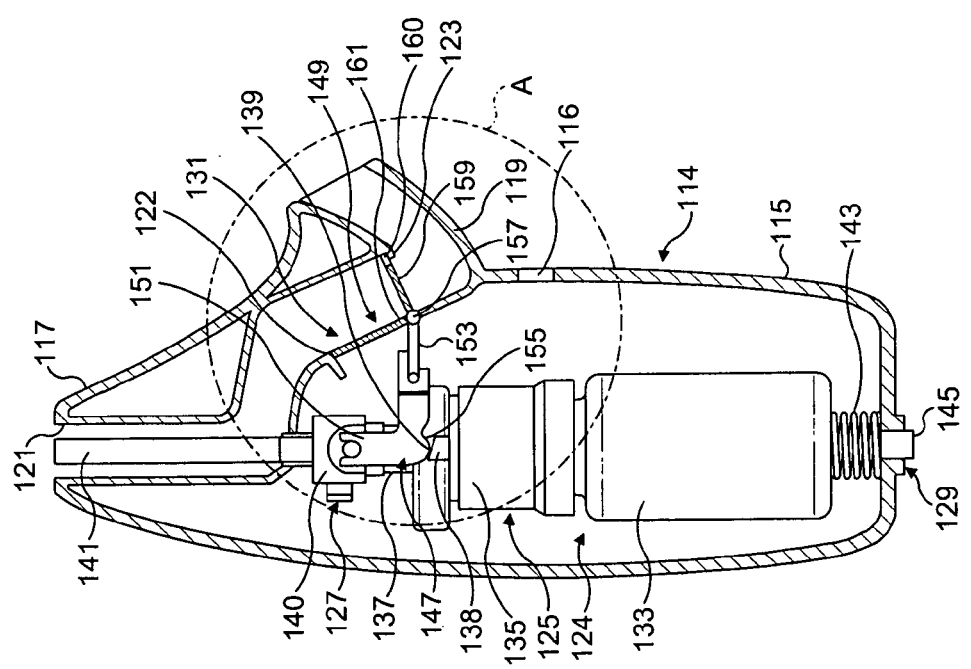

BREATH-ACTUATED NASAL DELIVERY DEVICE

This application is a national phase of International Application No. PCT/IB02/03849 filed Sep. 6, 2002 and published in the English language, and is a continuation-in-part of U.S. patent application Ser. No. 09/700,532 filed Nov. 15, 2000 now U.S. Pat. No. 6,715,485.

The present invention relates to a breath-actuated nasal delivery device for and a method of delivering a substance, in particular one of a liquid, as a suspension or solution, or a powder containing a medicament, especially systemic or topical pharmaceuticals, or a vaccine to the nasal airway of a subject.

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse affects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *Helicobacter pylori* infections which cause gastric ulcers.

To date, nasal medicaments have been primarily delivered as drops or by mechanical nasal spray pumps. With mechanical spray pumps, the mean particle size is typically between 40 µm and 80 µm in order to prevent the inhalation of delivered particles. In general, particles smaller than 10 µm will bypass the nose and can be inhaled. Indeed, the new FDA guidelines require that the fraction of particles less than 10 µm be at most 5%.

Whilst the provision of a spray having a larger mean particle size prevents the inhalation of the particles, these larger particles are not optimal for achieving a good distribution to the nasal mucosa.

The applicant has now recognized that the closure of the oropharyngeal velum during the delivery of a substance to the nasal airway prevents the possible inhalation of the substance, thereby enabling the delivery of an aerosol having a much smaller mean particle size than achieved by traditional nasal spray pumps. In this way, an aerosol can be generated which has an optimal particle size distribution.

A further advantage is that the nosepiece acts to expand the narrowest, anterior part of the nasal cavity and thereby reduces the unwanted high deposition in the anterior region of the nasal cavity which is lined by squamous epithelium.

In addition, the applicant has recognized that, by establishing a bi-directional flow through the nasal cavities as described in WO-A-00/51672, that is, an air flow which passes into one nostril, around the posterior margin of the nasal septum and in the opposite direction out of the other nostril, an aerosol having an optimal flow rate and timing can be generated. Furthermore, the bi-directional air flow advantageously acts to stimulate the sensory nerves in the nasal mucosa, thereby conditioning the subject for the delivery and providing a more comfortable delivery situation.

A yet further advantage is that the air flow acts to create a positive pressure inside the nasal passages connected in series, which tends to expand and widen narrow and congested regions.

A still yet further advantage is that the two-point fixation of the device in the nose with a well-fitting nozzle and in the mouth provides a much more stable and reproducible positioning of the device as compared to traditional spray pumps. Thus, in addition to improved deposition and reproducibility, the new concept provides a more user-friendly and intuitive nasal delivery method.

Furthermore, the delivery device, in being pre-primed and actuatable by the oral exhalation breath of a subject, does not require the application of an actuation force by the subject at the time of actuation. Traditionally, mechanical liquid delivery pumps are operated by the manual compression of a chamber containing a volume of liquid to expel a flow of a metered volume of liquid, and mechanical powder delivery pumps are operated by the manual compression of a chamber containing a volume of air to drive and expel a flow of a metered amount of a dry powder. Such operation requires a relatively high actuation force, typically of the order of 50 N, which high force often leads to significant movement of the delivery device, it being very difficult to maintain a delivery device stationary when attempting to apply a high actuation force. Movement of the delivery device, both in the positioning and orientation of the nozzle, will lead to poor reproducibility, dose accuracy and patient compliance. In being pre-primed and actuatable by the oral exhalation breath of a subject, the delivery device of the present invention overcomes this problem.

In addition, by not requiring a subject to apply an actuation force at the instance of delivery, the delivery device provides for the same actuation force in each delivery, and also provides for delivery at an optimal pressure and/or flow rate, and the delivery of substance having an optimized particle size distribution.

Yet furthermore, in providing for the closure of the oropharyngeal velum of a subject, substance is prevented from entering the lower airway, and also, in a preferred embodiment, bi-directional delivery can be achieved through the nasal cavities.

It will be appreciated that the nasal delivery devices of the present invention are quite different to inhalation devices which provide for inhalation into the lower airway.

Inhalation devices have been used for a long time for the inhalation of medicaments in the treatment of lower airway pathologies.

One such inhalation device is the pressurized metered dose inhaler (pMDI). In such inhalers, a metered dose of medicament is released as an aerosol by actuating an aerosol canister, with the particle sizes of the aerosol being required to be small, typically less than 5 µm, in order to reach the distal parts of the lower airway. One drawback with traditional pMDIs is that the subject must co-ordinate inhalation with the aerosol release in order to deliver the aerosolized medicament effectively to the lower airway. Inadequate co-ordination represents a considerable problem, significantly reducing both lung deposition and reproducibility. Another drawback with traditional pMDIs is the use of chlorine-containing compounds as the propellant gas, as such gases are not environmentally friendly and have been demonstrated to destroy the ozone layer. Recently, in order to alleviate these drawbacks, pMDIs have been developed which use an alternative propellant gas, this being a hydrofluoroalkane (HFA), and incorporate a breath-actuation mechanism which provides for actuation of the aerosol canister on inhalation by the subject.

Another such inhalation device is the dry powder inhaler, such as the Turbohaler® inhaler as supplied by AstraZeneca and the Discus® inhaler as supplied by GSK. These dry powder inhalers do not require co-ordination of delivery and inhalation and can improve deposition to the lower airways.

Bi-directional nasal drug delivery is achieved by directing an exhaled air flow through the nasal passages in series, or by triggering another flow source to create such an air flow, whereas breath actuation of pulmonary drug delivery is by inhalation into a closed expanding volume, that is, the lungs. For bi-directional nasal delivery, it is desirable to establish the air flow before the drug is released, whereas for inhalation, the release is best achieved at the very beginning of inspiration to reach the most distal parts of the lungs.

Increased airway resistance in pathological conditions, both in the pulmonary and nasal airways, is a challenge. In inhalation devices, an air flow is created by the inspiratory muscles creating a negative pressure inside the chest. In this way, air is sucked through the device and into the airways. For pulmonary drug delivery, it is essential that the triggering occurs, not only early, but also at a relatively low flow to ensure release in subjects with a very low lung capacity. Furthermore, the releasing action should require as little energy as possible, as any resistance in the device will impede free inhalation. Still most subjects, even patients with lung diseases, will be able to achieve a flow rate of 25 L/min which is typically required to trigger the release from a pMDI device.

For the nose, the situation is more complex and in many ways different. The expiratory muscles in the thorax produce the exhaled air flow used to trigger release, and this air flow is then directed through the device and into the nasal passages in series, or used to trigger another flow source. Thus, the triggering air flow is completely reversed as compared to pulmonary breath actuation, and the air flow is directed into another airway/compartment separated from the lower airways.

Furthermore, the nose geometry is designed to humidify, warm and filter the inspired air to protect the lower airways. The resistance in the nose alone equals 50% of the total airway resistance, and the resistance may increase immensely when congested. Owing to the high anterior resistance, turbulence occurs just posterior to the constriction, increasing deposition in this region. To achieve a better distribution to larger and more posterior parts of the nasal mucosa, it is envisaged to be advantageous to have the drug released at a lower flow in a congested nose and at a higher flow in a open nose. This requires a system which can be released not only by flow, but also by pressure. Such release is essential for an efficient and reliable exhalation-triggered nasal drug delivery. In this regard, reference is made to co-pending UK application nos 0104692.9 and 0114272.8, the contents of which are hereby incorporated by reference. The two main triggering modes, flow and pressure, are to certain extent overlapping. They can be incorporated in one single mechanism or provided as separate mechanisms. However, the nose may become completely blocked, in particular during colds and allergic attacks. In this situation, it becomes impossible to establish a bi-directional air flow, but still it is desirable and necessary to deliver drugs to the nose. Furthermore, for some purposes, the exhaled air flow may only be used to trigger release from a pMDI or a mechanical spray pump. Again, the triggering may be mainly flow dependent or mainly/strictly pressure dependent.

Thus, the requirements for a breath-actuation mechanism for nasal drugs are different from those for inhaled drugs. The main features of exhalation-triggered nasal drug release are (i) triggering of drug release by exhalation, (ii) triggering when a bi-directional flow is established, (iii) triggering at a flow rate which provides optimal distribution, (iv) triggering in a very congested and even completely blocked nose, (v) triggering of external flow sources (pMDI), and (vii) triggering of a spray pump aerosol even in the absence of bi-directional flow.

In one aspect the present invention provides a breath-actuated nasal delivery device, comprising: a mouthpiece through which a user in use exhales to actuate the delivery device; a nosepiece for fitting to a nostril of the user through which a substance is in, use delivered; a substance supply unit actuatable to deliver a dose of a substance through the nosepiece; a loading unit operable to load the substance supply unit with an actuation force; and a release mechanism for enabling actuation of the substance supply unit in response to exhalation by the user through the mouthpiece; wherein the release mechanism comprises a locking unit which is movable between a locking configuration in which the substance supply unit is locked in a non-actuated position when loaded by the loading unit and a release configuration in which the substance supply unit is actuatable by the loading unit, and a trigger member for releasing the locking unit from the locking configuration to the release configuration in response to exhalation by the user through the mouthpiece and thereby enabling actuation of the substance supply unit.

In one embodiment the trigger member comprises a flow-sensitive element in fluid communication with the mouthpiece.

In one embodiment the flow-sensitive element comprises a vane.

Preferably, the flow-sensitive element includes an aperture which allows for a predeterminable air flow thereover prior to actuation.

Preferably, the flow-sensitive element is one or both of shaped and sized such as to allow for a predeterminable air flow thereover prior to actuation.

In another embodiment the trigger member comprises a pressure-sensitive element in fluid communication with the mouthpiece.

In one embodiment the pressure-sensitive element comprises a vane.

In another embodiment the pressure-sensitive element comprises a flexible membrane.

Preferably, the flexible membrane comprises a resilient membrane.

In a further embodiment the pressure-sensitive element comprises a flexible membrane in fluid communication with the mouthpiece and a vane operable by the flexible membrane.

Preferably, the flexible membrane comprises a resilient membrane.

Preferably, the delivery device further comprises: a pressure-sensitive sealing unit disposed downstream of the trigger member and being operable to vent an air flow developed by the user on exhalation through the mouthpiece to atmosphere, the sealing unit being normally closed and operable such as to be opened on generation of a predeterminable pressure thereat.

In one embodiment the sealing unit comprises an annular seal, a sealing member movable between a closed position in sealing engagement with the annular seal and an open position in which an air flow can flow through the annular seal, and a biasing element for normally biasing the sealing member to the closed position and enabling the sealing member to be opened on generation of a predeterminable pressure thereat.

In another embodiment the sealing unit comprises a flexible membrane which is movable between a closed position and an open position in which an air flow can flow thereby.

Preferably, the flexible membrane comprises a resilient membrane.

Preferably, the trigger member includes a pivot pin about which the same is rotatable, which pivot pin is engaged by the locking unit when in the locking configuration such that the locking unit is moved from the locking configuration to the release configuration on rotation of the pivot pin.

More preferably, the locking unit includes a first, support member which abuts the substance supply unit in the locking configuration and a second, link member which engages the pivot pin of the trigger member in the locking configuration, wherein the link member is movable in relation to the support member and configured to be moved on rotation of the pivot pin to move the locking unit from the locking configuration to the release configuration.

Yet more preferably, the link member is rotatably connected to the support member.

Still more preferably, the link member is configured to load the pivot pin radially.

In one embodiment the delivery device further comprises: a flow path fluidly connecting the nosepiece and the mouthpiece, whereby an air flow developed by exhalation by the user through the mouthpiece is delivered through the nosepiece.

In another embodiment the nosepiece and the mouthpiece are fluidly isolated such that an air flow developed by exhalation by the user through the mouthpiece is not delivered through the nosepiece.

In one embodiment the substance supply unit comprises a nebulizer for supplying an aerosol.

In another embodiment the substance supply unit comprises an aerosol canister for supplying an aerosol.

In a further embodiment the substance supply unit comprises a delivery pump unit for supplying one of an aerosol or a jet.

In one preferred embodiment the delivery pump unit comprises a liquid pump unit for supplying a liquid aerosol.

In another preferred embodiment the delivery pump unit comprises a powder pump unit for supplying a powder aerosol.

In a yet further embodiment the substance supply unit comprises a powder delivery unit for delivering a powder aerosol.

Preferably, the delivery device further comprises: a flow-control mechanism disposed upstream of the trigger member to at least restrict an air flow to the trigger member such as to prevent actuation of the release mechanism on exhalation by the user through the mouthpiece where the delivery device is being improperly operated.

In one embodiment the flow-control mechanism is configured to at least restrict the air flow to the trigger member where the delivery device is in an improper orient.

In another embodiment the flow-control mechanism is configured to at least restrict the air flow to the trigger member where the air flow developed by the user has a rate exceeding a predeterminable threshold value.

More preferably, the flow-control mechanism comprises a flow channel section which includes a recess, and a ball which is movably, captively disposed within the flow channel section, the ball normally, with proper operation of the delivery device, resting in the recess such as to allow a sufficient air flow to the trigger member as to enable actuation of the release mechanism, and being moved to at least partially block the flow channel section where the delivery device is being improperly operated such as to prevent actuation of the release mechanism.

In another aspect the present invention provides a breath-actuated nasal delivery device, comprising: a mouthpiece through which a user in use exhales to actuate the delivery device; a nosepiece for fitting to a nostril of the user through which a substance is in use delivered and being in fluid communication with the mouthpiece; a substance supply unit actuatable to deliver a dose of a substance through the nosepiece; a release mechanism for enabling actuation of the substance supply unit in response to exhalation by the user through the mouthpiece; and a flow-control mechanism disposed upstream of the trigger member to at least restrict an air flow to the trigger member such as to prevent actuation of the release mechanism on exhalation by the user through the mouthpiece where the delivery device is being improperly operated.

In one embodiment the flow-control mechanism is configured to at least restrict the air flow to the trigger member where the delivery device is in an improper orient.

In another embodiment the flow-control mechanism is configured to at least restrict the air flow to the trigger member where the air flow developed by the user has a rate exceeding a predeterminable threshold value.

Preferably, the flow-control mechanism comprises a flow channel section which includes a recess, and a ball which is movably, captively disposed within the flow channel section, the ball normally, with proper operation of the delivery device, resting in the recess such as to allow a sufficient air flow to the trigger member as to enable actuation of the release mechanism, and being moved to at least partially block the flow channel section where the delivery device is being improperly operated such as to prevent actuation of the release mechanism.

In a further aspect the present invention provides a release mechanism for enabling actuation of a substance supply unit, the release mechanism comprising: a locking unit which is movable between a locking configuration in which the substance supply unit is locked in a non-actuated position and a release configuration in which the substance supply unit is actuatable; and a trigger member for releasing the locking unit from the locking configuration to the release configuration in response to a gas flow thereat, wherein the trigger member includes a pivot pin about which the same is rotatable, which pivot pin is engaged by the locking unit when in the locking configuration such that the locking unit is moved from the locking configuration to the release configuration on rotation of the pivot pin.

Preferably, the locking unit includes a first, support member which abuts the substance supply unit in the locking configuration and a second, link member which engages the pivot pin of the trigger member in the locking configuration, wherein the link member is movable in relation to the support member and configured to be moved on rotation of the pivot pin to move the locking unit from the locking configuration to the release configuration.

Preferably, the link member is rotatably connected to the support member.

Preferably, the link member is configured to load the pivot pin radially.

In a still further aspect the present invention provides a breath-actuated nasal delivery pump for delivering a liquid containing a substance to a nasal cavity of a user.

In one embodiment the delivery pump is a spray pump and the liquid is delivered as a liquid spray.

In another embodiment the delivery pump is a jet pump and the liquid is delivered as a liquid jet.

Preferred embodiments of the present invention will now be described hereinbelow by way of example only with reference to the accompanying drawings, in which:

FIG. 1 schematically illustrates the anatomy of the upper respiratory tract of a human subject;

FIG. 4(a) illustrates one side view of the substance delivery assembly of the nasal delivery device of FIG. 2(a);

FIG. 4(b) illustrates another side view of the substance delivery assembly of the nasal delivery device of FIG. 2(a);

FIG. 4(c) illustrates a part-sectional other side view of the substance delivery assembly of the nasal delivery device of FIG. 2(a);

FIG. 7(a) illustrates a part cut-away perspective view of the nasal delivery device of FIG. 2(a) in an inoperative, rest configuration;

FIG. 7(b) illustrates a part cut-away perspective view of the nasal delivery device of FIG. 2(a) in a loaded, operable configuration;

FIG. 8(a) illustrates a part-sectional view of a nasal delivery device in accordance with a second embodiment of the present invention, illustrated in an inoperative, rest configuration;

FIG. 8(b) illustrates a part-sectional view of the nasal delivery device of FIG. 8(a) in a loaded, operable configuration;

Figure 14A:
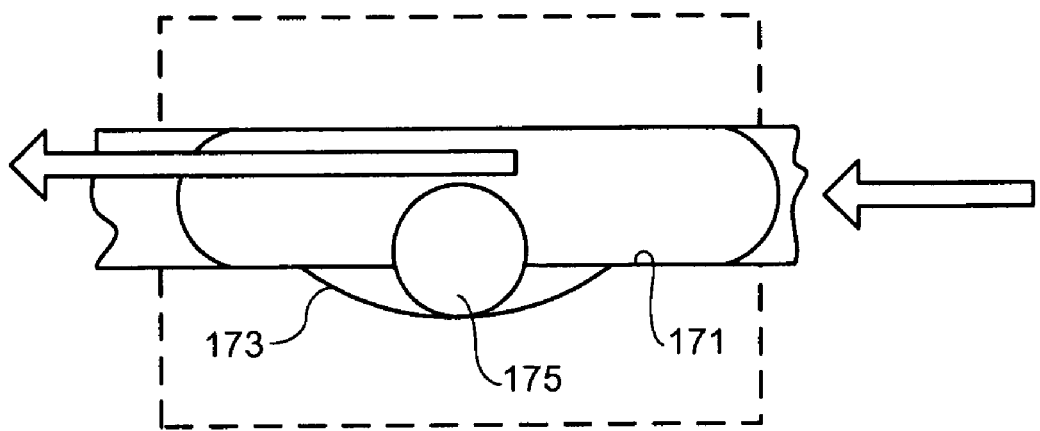
Figure 15A:
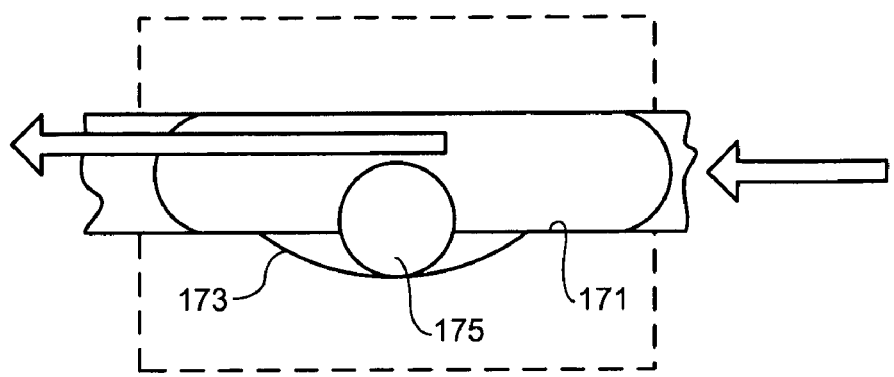
Figure 15B:
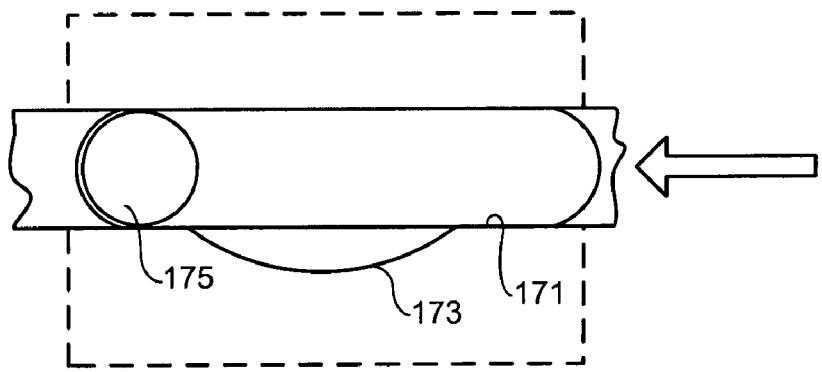
Figure 15C:
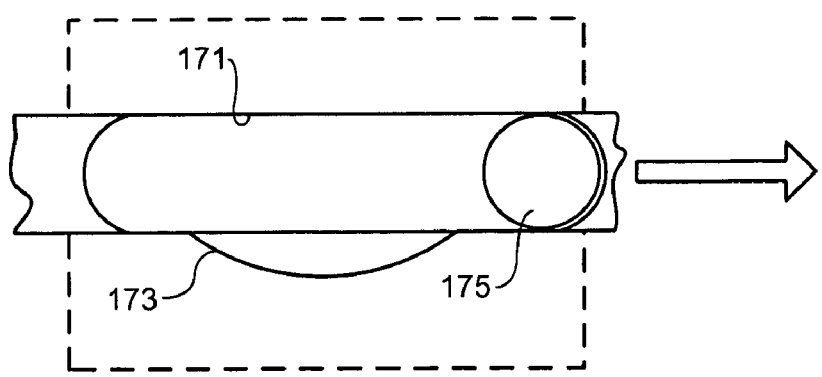

FIGS. 14(a) and (b) illustrate a flow-control mechanism in accordance with an embodiment of the present invention; and FIGS. 15(a) to (c) illustrate the function of the flow-control mechanism of FIGS. 14(a) and (b) where a user exhales rapidly or inhales therethrough.

FIGS. 2 to 7 illustrate a breath-actuated nasal delivery device in accordance with a first embodiment of the present invention.

The delivery device comprises a housing unit 14, in this embodiment provided by first and second housing parts 14a, 14b, which defines a main body 15 which is typically gripped in the hand of a user, a nosepiece 17 for fitting to a nostril of a user and a mouthpiece 19 through which the user exhales to actuate the delivery device, and a guide member 20 which, in this embodiment, together with the housing unit 14 defines a main flow path 21 between the nosepiece 17 and the mouthpiece 19.

The main body 15 includes first and second cam recesses 22, 22 on opposed sides at a lower end thereof for receiving respective ones of the engagement elements 55, 55 of a loading member 51, as will be described in more detail hereinbelow. The cam recesses 22, 22 each comprise a cam surface 23 which engages the cam element 57 of a respective one of the engagement elements 55, 55 of the loading member 51, and a lug aperture 24 adjacent the cam surface 23 through which extends the lug 58 of the respective one of the engagement elements 55, 55 of the loading member 51.

The main body 15 includes at least one external venting aperture, in this embodiment a plurality of external venting apertures 25, 25 which provide for a vent to atmosphere, and further defines a gas venting path 26 which can provide a fluid communication path between the external venting apertures 25, 25 and the main flow path 21 at a location downstream of the vane 89 of a trigger member 61, as will be described in more detail hereinbelow. As will be described in more detail hereinbelow, the gas venting path 26 is normally isolated from the main flow path 21 by a pressure-sensitive sealing unit 93, and is brought into fluid communication with the main flow path 21 by opening the pressure-sensitive sealing unit 93 where a sufficient flow rate cannot be developed through the main flow path 21, for example, as a result of the nasal passage of the user being congested, and the pressure in the main flow path 21 exceeds a predetermined threshold pressure.

In this embodiment the nosepiece 17 has a tapering section which narrows to the distal end thereof and acts, when inserted, typically from about 1 to 2 cm, into the anterior part of a nasal cavity, to expand the narrow nasal valve of the nasal cavity and provide a fluid-tight seal.

In this embodiment the mouthpiece 19 is configured to be gripped in the lips of a user. In an alternative embodiment the mouthpiece 19 could be configured to be gripped by the teeth of a user and sealed by the lips of the user. In a preferred embodiment the mouthpiece 19 is specifically configured to have one or both of a shape and geometry which allows the delivery device to be gripped repeatedly in the same position, thereby providing for the nosepiece 17 to be reliably inserted in the same position in the nasal cavity.

The guide member 20 includes an arcuate section 27, adjacent which the distal end of the vane 89 of the trigger member 61 is movably disposed, and a vane stop 29 which defines the rest position of the vane 89 of the trigger member 61 when a locking assembly 59 is in the locking configuration. The provision of the vane stop 29 acts to prevent the actuation of a substance supply unit 31 on inhalation by the user, as will be described in more detail hereinbelow.

In this embodiment the main flow path 21 provides a fluid communication path between the nosepiece 17 and the mouthpiece 19 such that an exhalation breath of the user can provide for bi-directional flow through the nasal cavities as disclosed in WO-A-00/51672. In alternative embodiments there could be no fluid communication path between the nosepiece 17 and the mouthpiece 19 such that an exhalation breath of the user is not directed to the nasal cavities of the user. These alternative embodiments include those where substance is delivered in a separate gas flow, such as from a pressurized canister, for example, a pMDI canister.

The delivery device further comprises a breath-actuated substance delivery assembly 30 for delivering substance through the nosepiece 17 on exhalation by the user through the mouthpiece 19.

The substance delivery assembly 30 comprises a substance supply unit 31 for delivering a metered dose of a substance on actuation of the same, an outlet unit 32 which is fluidly connected to the substance supply unit 31 for delivering substance through the nosepiece 17, a loading mechanism 33 for loading the substance supply unit 31, and a release mechanism 34 for releasing the substance supply unit 31 from a loaded, non-actuated position to an actuated position on exhalation by the user through the mouthpiece 19.

In this embodiment the substance supply unit 31, as a mechanical pump, comprises a container 35 containing a volume of liquid containing a substance, a pump fitting 36 which includes a metering chamber and is connected to the container 35, and an outlet stem 37 which is movably disposed to the pump fitting 36 and through which liquid is delivered. In operation, a metered volume of liquid is delivered on relative movement of the pump fitting 36 and the outlet stem 37, in this embodiment movement of the pump fitting 36 in relation to the outlet stem 37, between a first position in which the outlet stem 37 is extended from the pump fitting 36 and a second position in which the outlet stem 37 is depressed into the pump fitting 36.

In this embodiment the substance supply unit 31 is a multidose device for enabling the delivery of a succession of metered doses of substance. In an alternative embodiment the substance supply unit 31 could be a single dose device for delivering a single metered dose of substance.

The outlet unit 32 comprises an outlet block 40 which is fluidly connected to the outlet stem 37 of the substance supply unit 31 and, in this embodiment, includes a valve and swirl chamber, and a delivery tube 41 from which a mist of fine droplets of the liquid is expelled on actuation of the substance supply unit 31. In an alternative embodiment the delivery tube 41 could be configured to provide for the delivery of a liquid jet.

The loading mechanism 33 comprises a loading unit 42 which comprises a biasing element 43, in this embodiment a resilient element, here a compression spring, and first and second retaining elements 44, 45 between which the biasing element 43 is disposed such as to loadable with an actuation force, which is sufficient to actuate the substance supply unit 31 when released, on compression of the same, in this embodiment by moving one, the lower, retaining element 44 relative to the other, upper, retaining element 45. In this embodiment the retaining elements 44, 45 are coupled by a link 47, here a nut and bolt, to constrain the expansion of the biasing element 43 and thereby pre-bias the biasing element 43 to a predetermined extent. In this embodiment the one, lower retaining element 44 includes first and second shoulders 49, 49 on opposed sides thereof which are engaged by the respective lugs 58, 58 of the engagement elements 55, 55 of the loading member 51, as will be described in more detail hereinbelow.

Figure 1:
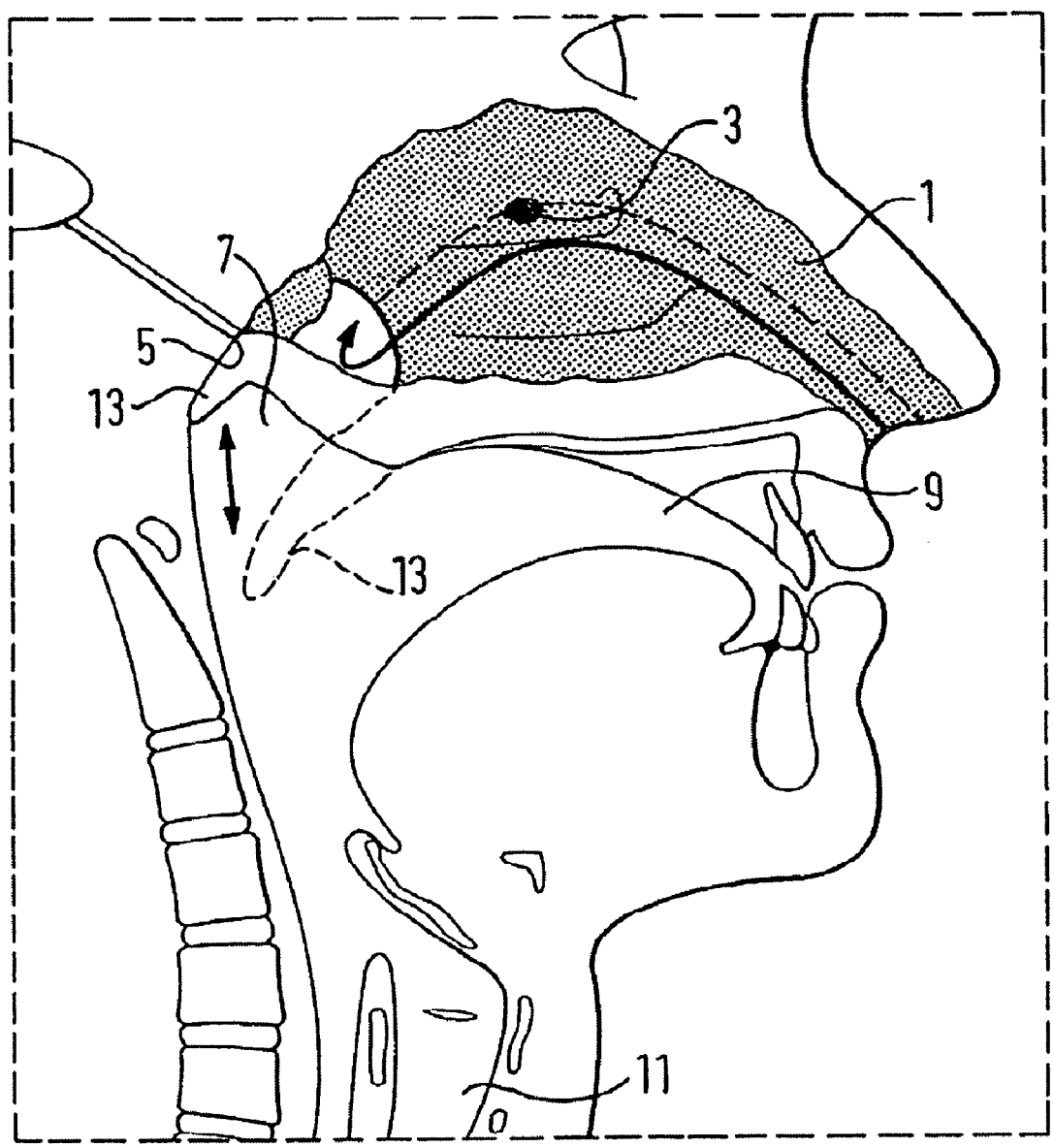
Figure 2A:
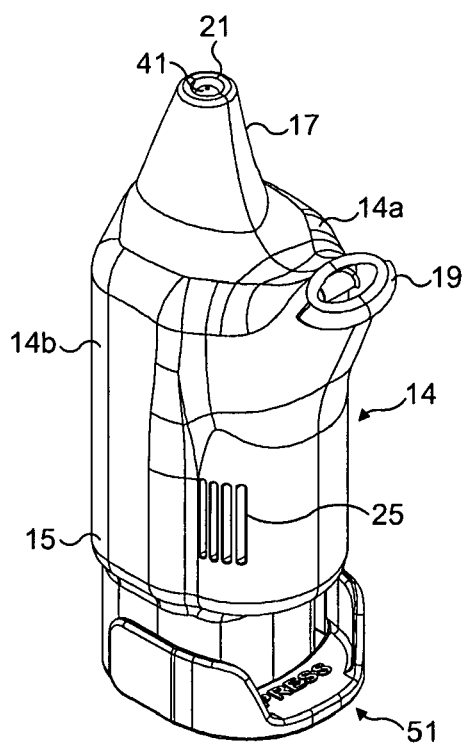
FIG. 2(a) illustrates a perspective view of a nasal delivery device in accordance with a first embodiment of the present invention.
Figure 2B:
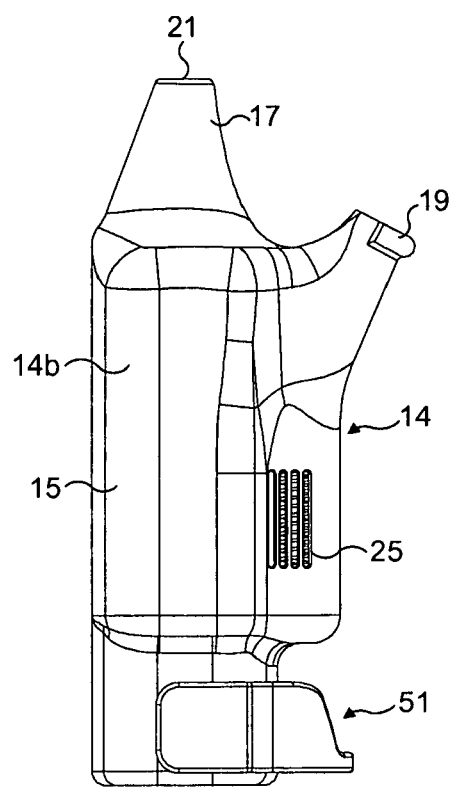
FIG. 2(b) illustrates one side view of the nasal delivery device of FIG. 2(a)
Figure 2C:
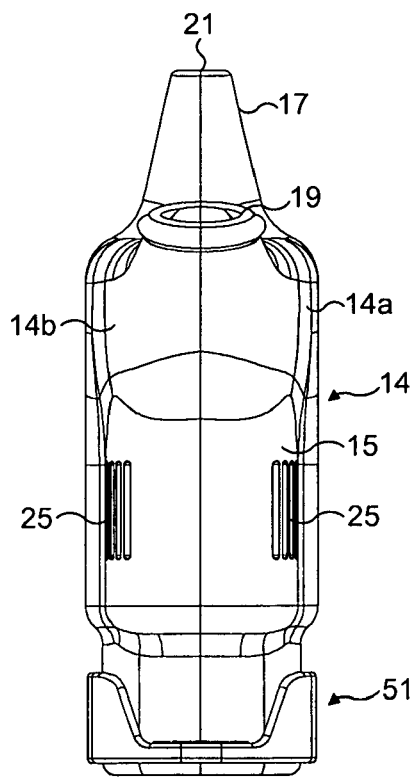
FIG. 2(c) illustrates another side view of the nasal delivery device of FIG. 2(a)
Figure 2D:
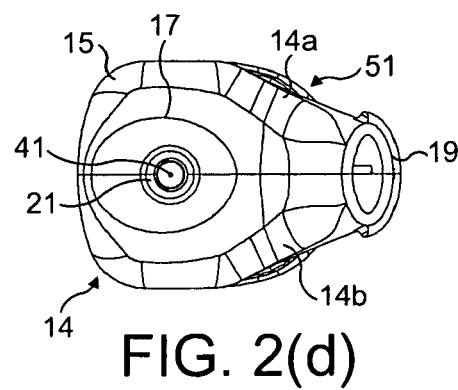
FIG. 2(d) illustrates a plan view of the nasal delivery device of FIG. 2(a)
Figure 3:
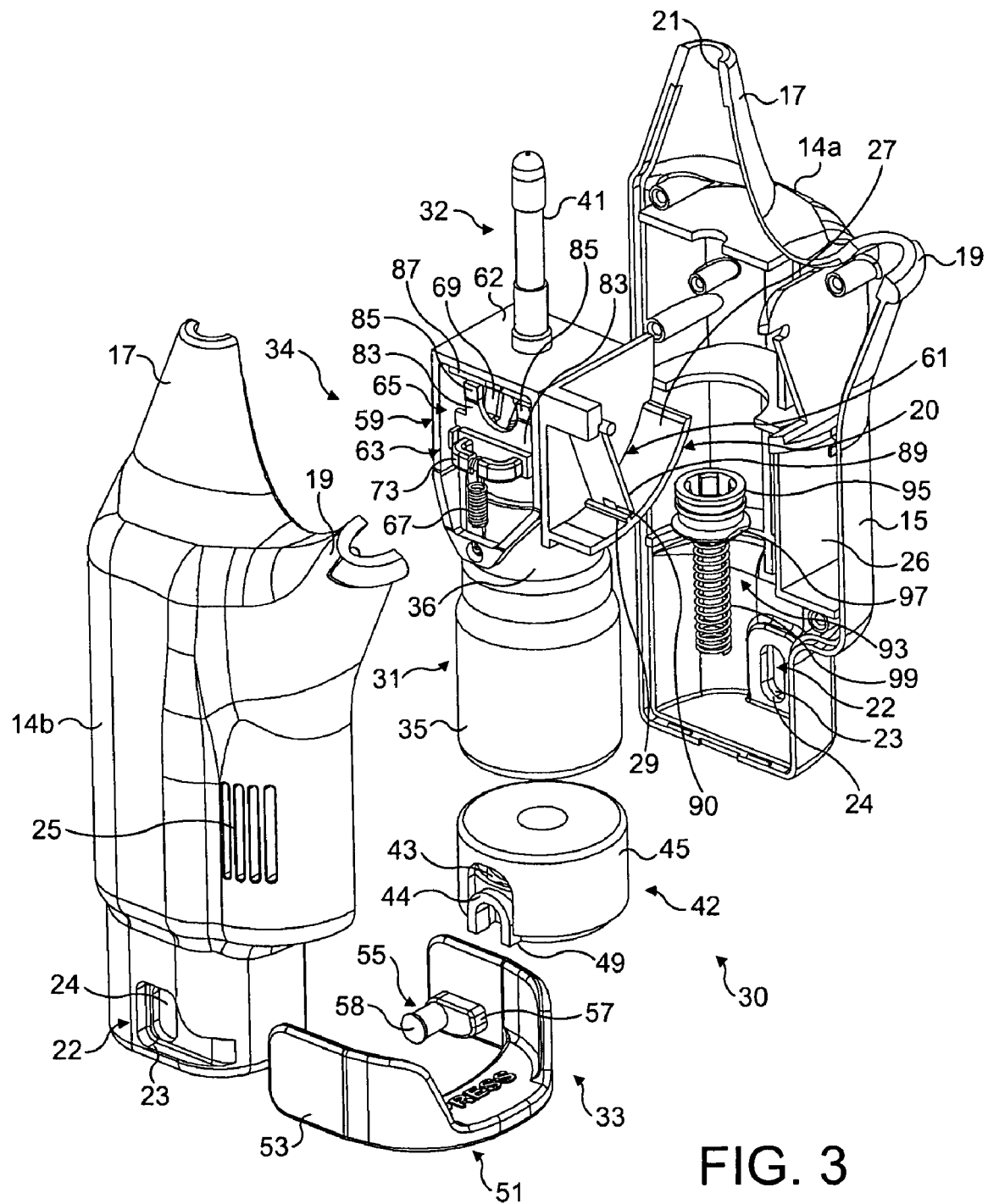
FIG. 3 illustrates a part-exploded perspective view of the nasal delivery device of FIG. 2(a)
Figure 4D:
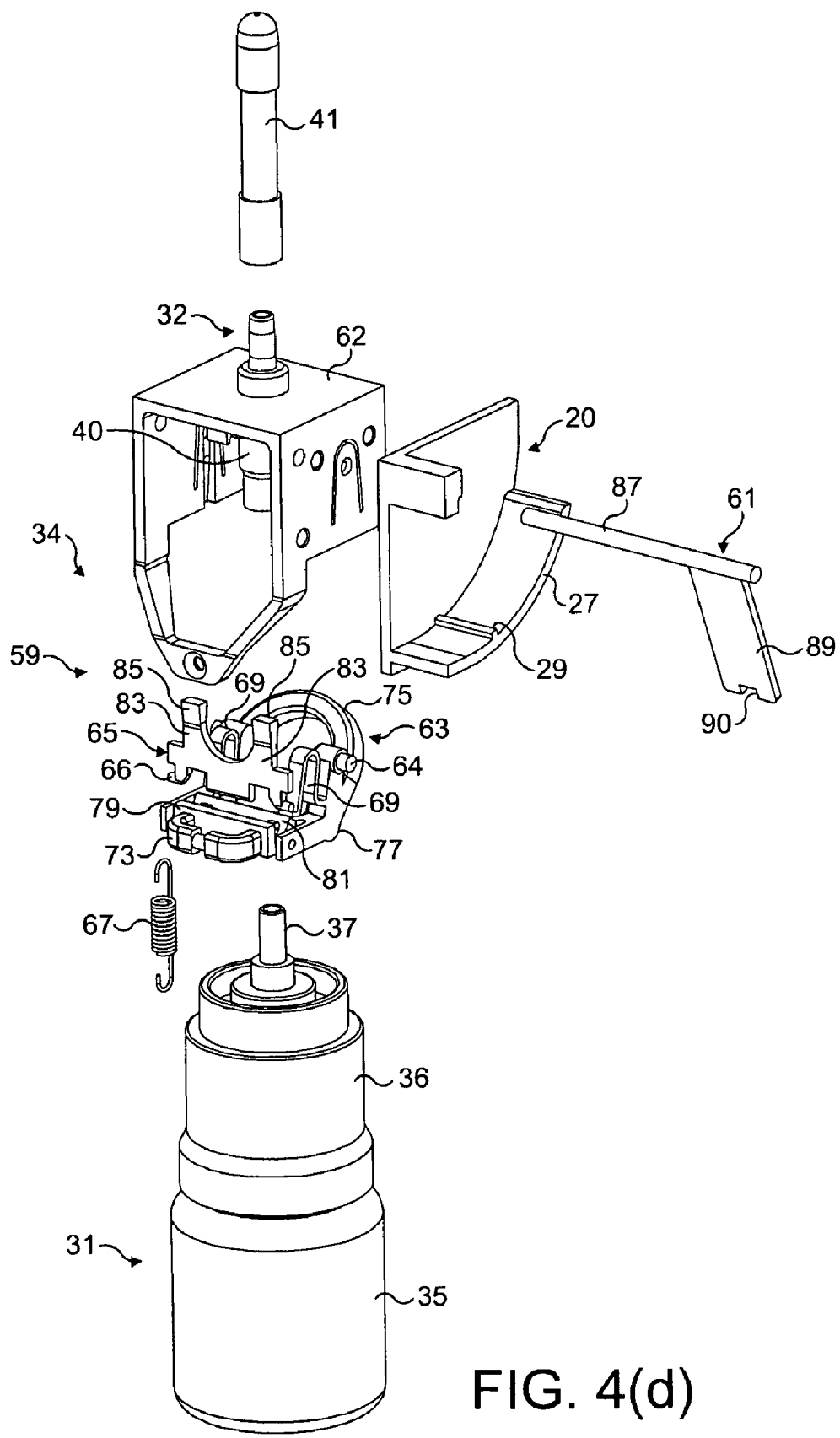
FIG. 4(d) illustrates an exploded perspective view of the substance delivery assembly of the nasal delivery device of FIG. 2(a)
Figure 5C:
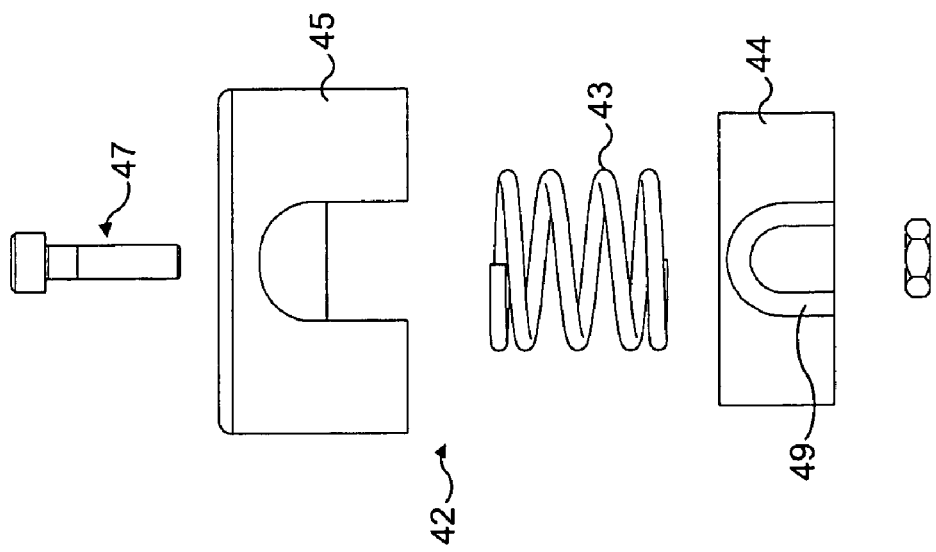
FIG. 5(c) illustrates an exploded side view of the loading unit of FIG. 5(a)
Figure 5B:
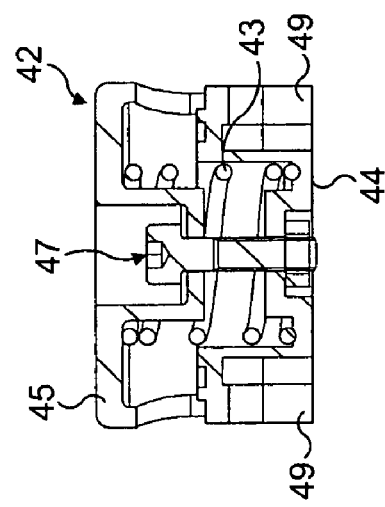
FIG. 5(b) illustrates a vertical sectional view through the loading unit of FIG. 5(a)
Figure 5A:
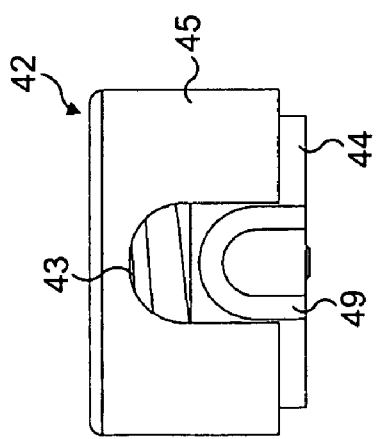
FIG. 5(a) illustrates a side view of the loading unit of the loading mechanism of the substance delivery assembly of the nasal delivery device of FIG. 2(a)
Figure 6C:
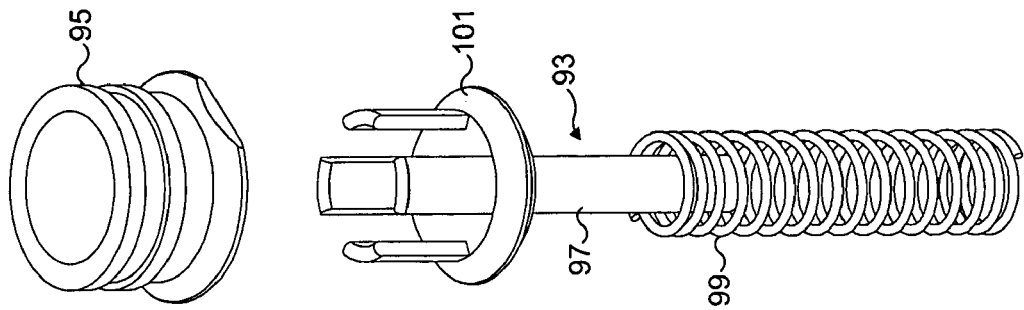
FIG. 6(c) illustrates an exploded perspective view of the pressure-sensitive release mechanism of FIG. 6(a)
Figure 6B:
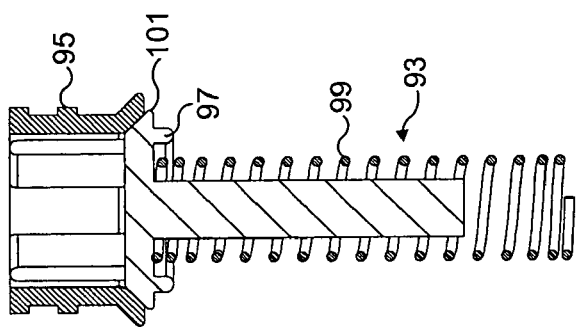
FIG. 6(b) illustrates a vertical sectional view of the pressure-sensitive release mechanism of FIG. 6(a)
Figure 6A:
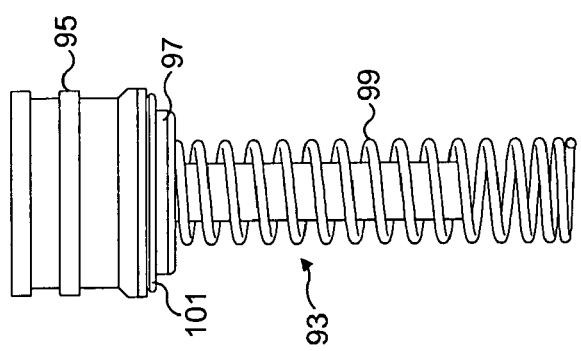
FIG. 6(a) illustrates a side view of the pressure-sensitive release mechanism of the nasal delivery device of FIG. 2(a)
Figure 7D:
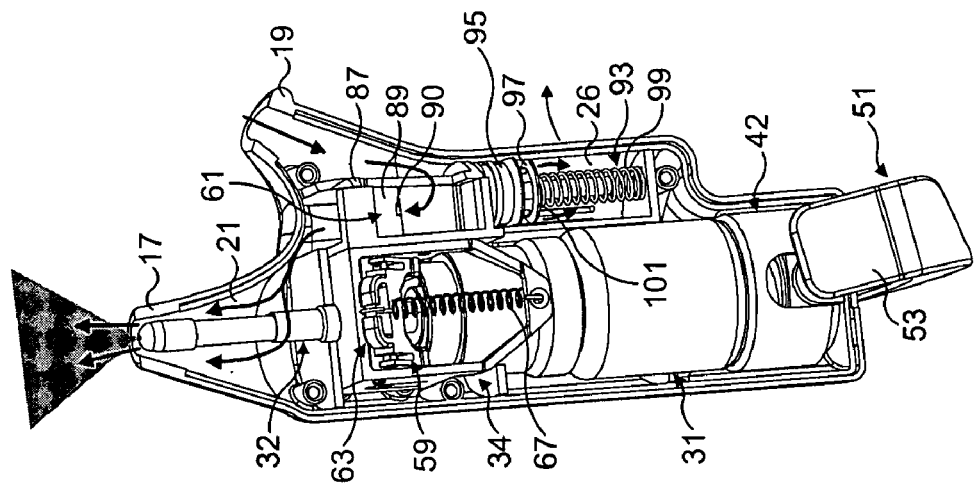
FIG. 7(d) illustrates a part cut-away perspective view of the nasal delivery device of FIG. 2(a) where operated in another mode of operation.

The loading mechanism 33 further comprises a loading member 51 for loading the loading unit 42. In this embodiment the loading member 51 comprises a U-shaped lever 53 which is movable from a non-loading position, as illustrated in FIG. 7(a), to a loading position, as illustrated in FIG. 7(b), in which the loading member 51 acts to load the loading unit 42 by biasing the same against the bottom end of the container 35 of the substance supply unit 31.

The loading member 51 includes first and second engagement elements 55, 55 which are disposed in opposed relation at the respective ends of the lever 53 and are located in respective ones of the cam recesses 22, 22 in the main body 15 of the body unit 14 and engage respective ones of the shoulders 49, 49 on the lower retaining element 44 of the loading unit 42.

The engagement elements 55, 55 each comprise a cam 57 which is located at a respective one of the cam surfaces 23, 23 of the cam recesses 22, 22 in the main body 15 of the body unit 14, and a lug 58 which extends through a respective one of the lug apertures 24, 24 of the cam recesses 22, 22 in the main body 15 of the body unit 14 and engages a respective one of the shoulders 49, 49 on the lower retaining element 44 of the loading unit 42. The cams 57, 57 are configured such that, on moving the lever 53 from the non-loading, rest position to the loading position, the lugs 58, 58 are driven, in this embodiment upwards, towards the lower retaining element 44 of the loading unit 42 such as to move the lower retaining element 44 of the loading unit 42 relative to the upper retaining element 45 of the loading unit 42 which is constrained by the bottom end of the container 35 of the substance supply unit 31, and thereby load the loading unit 42.

The release mechanism 34 comprises a locking assembly 59 which acts to lock the substance supply unit 31 in the non-actuated position, in this embodiment by preventing movement of the pump fitting 36 relative to the outlet stem 37 of the substance supply unit 31, until actuation of the release mechanism 34, and a trigger member 61 which is coupled to the locking assembly 59 and disposed at the mouthpiece 19 such as to support the locking assembly 59 until acted upon by an oral exhalation breath of a user.

In this embodiment the locking assembly 59 comprises a body member 62 which is fixed to the outlet block 40 of the outlet unit 32, a first, support member 63, which is hinged, in this embodiment about a hinge axis 64 to the body member 62, and engages the pump fitting 36 of the substance supply unit 31 in the locked position, a second, link member 65 which is hinged about a hinge axis 66 to the support member 63 between a first, locking position and a second, release position, and couples the support member 63 to the trigger member 61 when loaded, a first biasing element 67, in this embodiment a resilient element, here a tension spring, which is coupled to the body member 62 and the support member 63 such as to bias the support member 63 to the locking position, and a second biasing element 69, in this embodiment a resilient element, here compression springs, which is coupled to the support member 63 and the link member 65 such as to bias the link member 65 to the locking position.

In this embodiment the body member 62 includes a support member stop 70 which defines the locking position of the support member 63 where the support member 63 is biased to the locking position.

In this embodiment the hinge axis 64 of the support member 63 is offset from the longitudinal axis of the substance supply unit 31, such that, on release of the link member 65 from the locking position, the support member 63 is hinged upwardly by the action of the substance supply unit 31 being driven upwardly by the loading unit 42.

In this embodiment the support member 63 comprises first and second arms 73, 75 which extend in opposite directions and define an abutment surface 77 at the junction therebetween, and, with the support member 63 in the locking position, the abutment surface 77 engages the upper end of the pump fitting 36 of the substance supply unit 31, the first arm 73 extends over the upper end of the pump fitting 36 in a direction substantially orthogonal to the longitudinal axis of the substance supply unit 31 and the second arm 75 is inclined upwardly such as to engage the support member stop 70 on the body member 62.

In this embodiment the first arm 73 of the support member 63 includes a first link member stop 79 against which the link member 65 is biased in the locking position, with the first link member stop 79 being configured such that the link member 65 extends substantially orthogonally to the first arm 73 of the support member 63, and parallel to the longitudinal axis of the substance supply unit 31, when in the locking position.

In this embodiment the first arm 73 of the support member 63 includes a second link member stop 81 which acts to limit the rotation of the link member 65 when released from the locking position.

In this embodiment the link member 65 is a substantially rigid member which includes at least one, in this embodiment first and second engagement elements 83, 83 which engage the trigger member 61 when the link member 65 is in the locking position. In this embodiment the engagement elements 83, 83 each include an end cap 85 which is formed of a material of a high coefficient of friction, such as a rubber material, to provide for controlled engagement with the trigger member 61, and thereby prevent uncontrolled slipping from the trigger member 61. In an alternative embodiment the link member 65 could comprise a flexible, preferably resilient, element.

In this embodiment the trigger member 61 comprises a pivot pin 87 about which the trigger member 61 is rotatable between a first, supporting position in which the trigger member 61 engages the link member 65 in the locked position, and a second, released position in which the link member 65 is not supported, in having been caused to roll off the pivot pin 87, and released from the locking position.

In this embodiment the trigger member 61 further comprises a flow-sensitive vane 89 which extends from the pivot pin 87 and substantially closes the main flow path 21 when in the supporting position. In this embodiment the vane 89 is configured to engage the vane stop 29 on the arcuate section 27 of the guide member 20 when in the supporting position. In this embodiment the vane 89 includes an aperture 90 which acts to require a predetermined air flow through the main flow path 21 prior to releasing the trigger member 61 from the supporting position. Advantageously, with this configuration, a bi-directional air flow can be achieved through the nasal cavities prior to release of substance through the nosepiece 17. In an alternative embodiment, an air flow can be provided through the main flow path 21 prior to releasing the trigger member 61 from the supporting position by sizing the vane 89 to be of a size slightly smaller than the section of the main flow path 21, whereby an air flow of up to a predetermined flow rate can be developed about the vane 89 prior to driving the vane 89 such as to cause the trigger member 61 to be released from the supporting position.

The delivery device further comprises a pressure-sensitive sealing unit 93 which is configured normally to be closed, and thereby isolate the gas venting path 26 from the main flow path 21, such that the exhaled air flow of a user is directed through the main flow path 21, and be opened where the pressure in the main flow path 21 exceeds a predetermined threshold pressure such that an air flow can be developed over the vane 89 of the trigger member 61 which has a sufficient flow rate as to drive the vane 89 to actuate the locking assembly 59, with the exhaled air flow being vented through the external venting apertures 25, 25. As mentioned hereinabove, this configuration enables actuation of the release mechanism 34 in the event that the nasal passage of the user is so congested as to prevent the attainment of a sufficient flow rate as to drive the vane 89 of the trigger member 61 to actuate the release mechanism 34.

In this embodiment the sealing unit 93 comprises an annular seal 95 which is disposed such as to be a sealing fit at one, the upstream, end of the gas venting path 26, a sealing member 97 which is moveable between a first, normally closed position and a second, open position, and a biasing element 99, in this embodiment a resilient element, here a compression spring, for biasing the sealing member 97 to the closed position. The sealing member 97 includes an annular seat 101 and is movable between the closed position in which the annular seat 101 is in sealing engagement with the annular seal 95, with the annular seat 101 being maintained in sealing engagement with the annular seal 95 by the biasing element 99, and thereby closes the sealing unit 93 to isolate the gas venting path 26 from the main flow path 21, and the open position in which the sealing member 97 is driven out of sealing engagement with the annular seal 95 by the generation of a predetermined venting pressure in the main flow path 21, with the force generated by the venting pressure exceeding the biasing force applied by the biasing element 99, and thereby providing for fluid communication between the main flow path 21 and the gas venting path 26 such as to enable an air flow to be developed over the vane 89 of the trigger member 61 as required to actuate the release mechanism 34.

Operation of the delivery device will now be described hereinbelow.

Figure 7C:
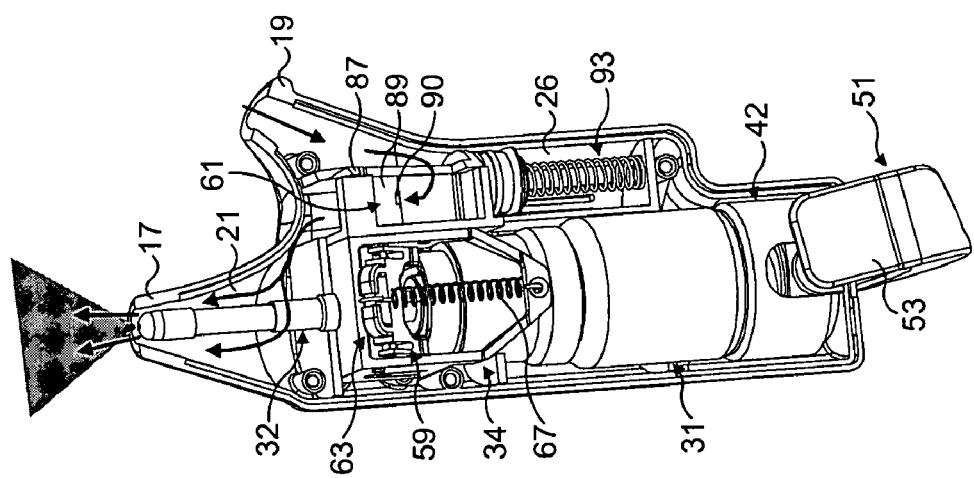
FIG. 7(c) illustrates a part cut-away perspective view of the nasal delivery device of FIG. 2(a) where operated in one mode of operation.

In operation, a user first takes the device, as illustrated in FIG. 7(*a*), and primes the device by rotating the loading member 51 of the loading mechanism 33 to the loaded position, as illustrated in FIG. 7(*b*). With the release mechanism 34 in the locked configuration, that is, with the abutment surface 77 of the supporting member 73 of the locking assembly 59 abutting the pump fitting 36, the loading unit 42 is biased against the bottom of the container 35 of the substance supply unit 31. The user then inserts the nosepiece 17 into one of the nasal cavities, grips the mouthpiece 19 with the lips, and exhales through the mouthpiece 19. Where an air flow can be established through the main flow path 21, by virtue of the aperture 90 in the vane 89 of the trigger member 61, a bi-directional air flow is developed through the nasal cavities. As illustrated in FIG. 7(*c*), with continued exhalation, the pressure differential across the vane 89 of the trigger member 61 increases, until such point that the pressure differential is such as to cause the rotation of the vane 89 and thereby the pivot pin 87 to which the vane 89 is attached. As illustrated in FIG. 7(*d*), where an air flow cannot be established through the nosepiece 17, for example, as a result of nasal congestion, the pressure in the main flow path 21 increases, until such point that the pressure acts to open the sealing unit 93, in this embodiment by driving the sealing member 97 from the annular seal 95, at which point an air flow is established via the gas venting path 26 and the external venting apertures 25, 25 to atmosphere, which air flow is such as to cause the rotation of the vane 89 and thereby the pivot pin 87 to which the vane 89 is attached. This rotation of the pivot pin 87 is such as to cause the movement of the link member 65 of the locking assembly 59, which link member 65, once no longer abutting the pivot pin 87 and supporting the locking assembly 59 in the locking configuration, allows for the movement, under the action of the loading unit 42, of the container 35 and the pump fitting 36 coupled thereto to actuate the substance supply unit 31 and deliver a metered volume of liquid from the delivery tube 41 of the outlet unit 32.

Figure 8C:
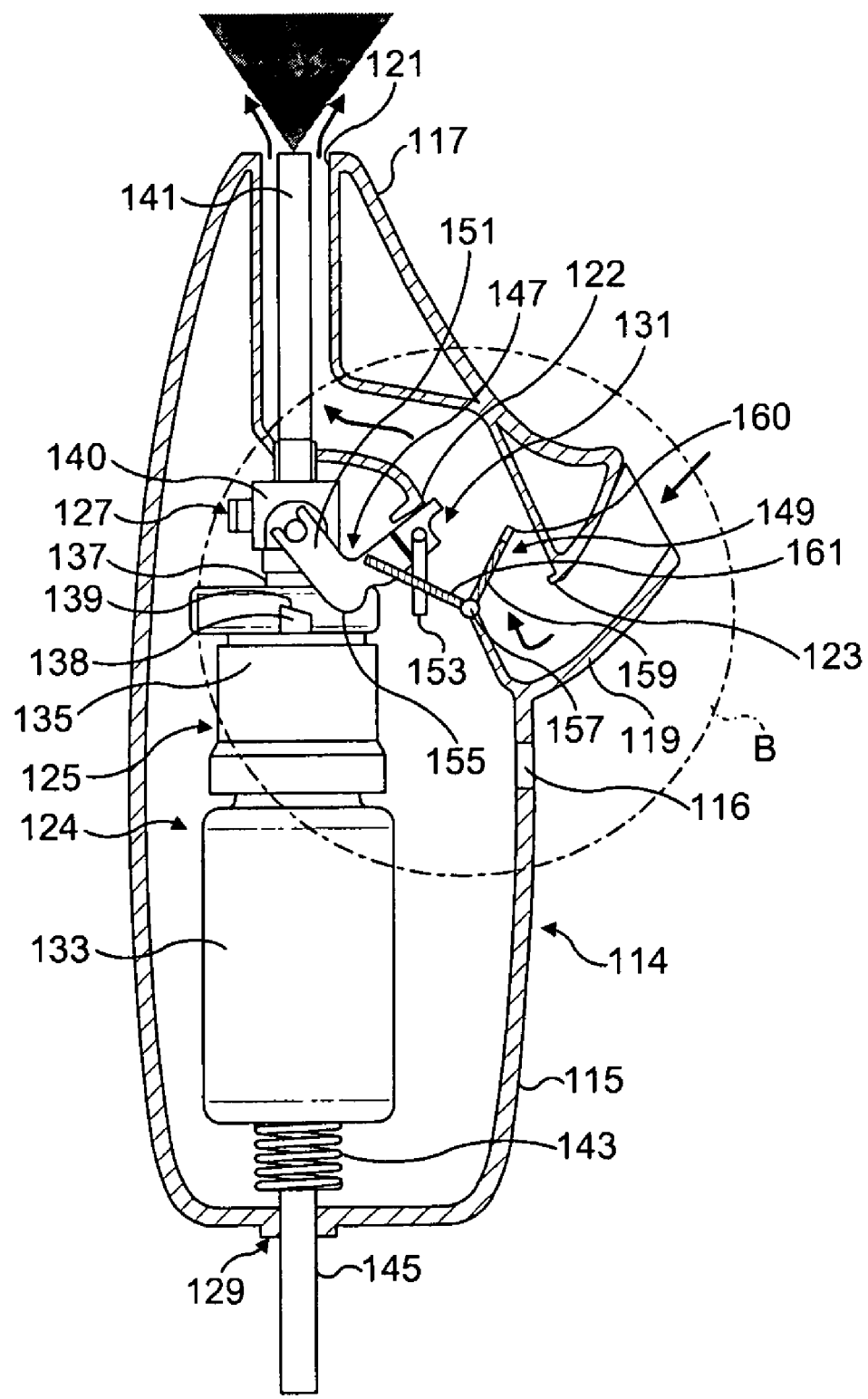
FIG. 8(c) illustrates a part-sectional view of the nasal delivery device of FIG. 8(a) in an actuated configuration.
Figure 9A:
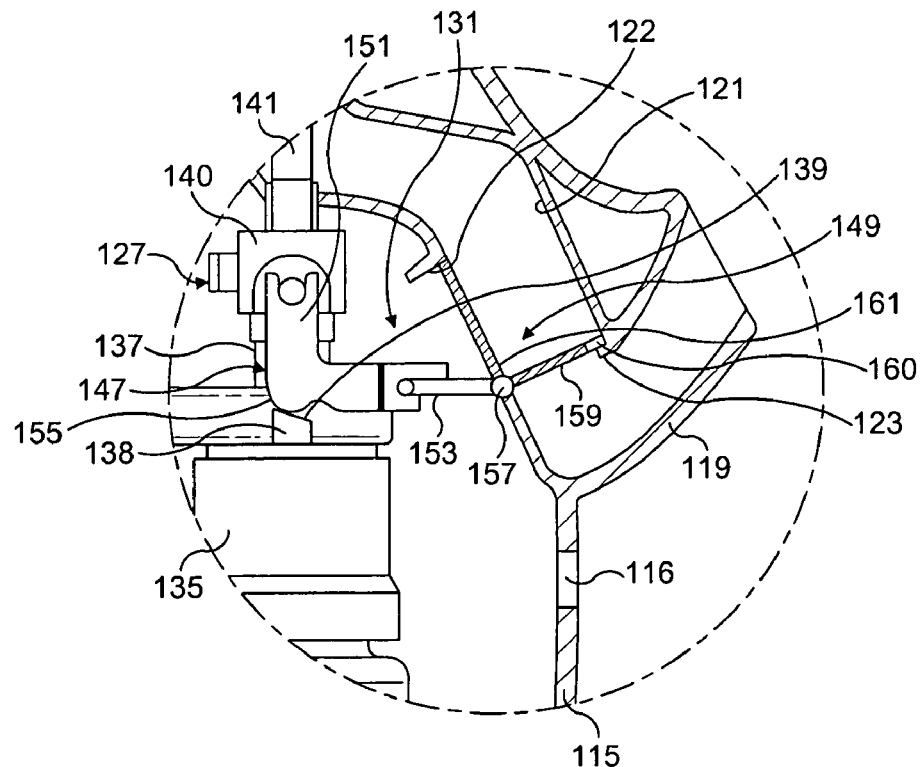
FIG. 9(a) illustrates in enlarged scale region A of FIG. 8(a)
Figure 9B:
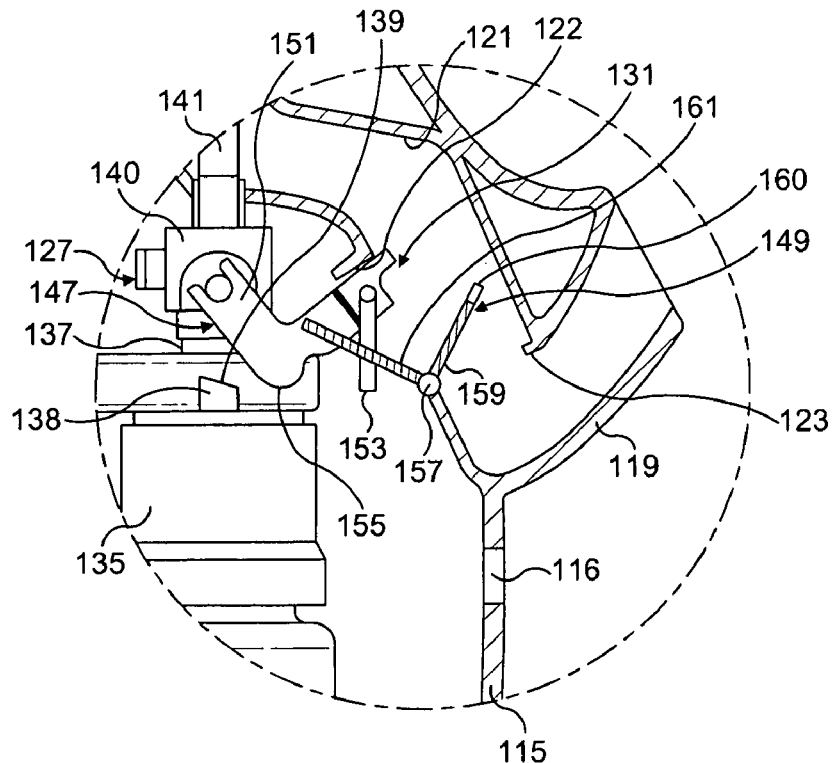
FIG. 9(b) illustrates in enlarged scale region B of FIG. 8(c)

FIGS. 8 and 9 illustrate a breath-actuated nasal delivery device in accordance with a second embodiment of the present invention.

The delivery device comprises a housing unit 114 which comprises a main body 115, a nosepiece 117 for fitting to a nostril of a user, and a mouthpiece 119 through which the user exhales to actuate the delivery device.

The main body 115 includes an aperture 116 for enabling any air flow thereinto to escape therefrom.

The main body 115 defines a main flow path 121 which provides a fluid communication path between the nosepiece 117 and the mouthpiece 119, and through which a substance is delivered to the nasal cavity of the user. The main flow path 121 includes an aperture 122 and an abutment 123 therein, the purpose of which will become apparent hereinbelow. In this embodiment the main flow path 121, in fluidly communicating the nosepiece 117 to the mouthpiece 119, is such that an exhalation breath of the user can provide for bi-directional flow through the nasal cavities as disclosed in WO-A-00/51672. In alternative embodiments there could be no fluid communication path between the nosepiece 117 and the mouthpiece 119 such that an exhalation breath of the user is not directed to the nasal cavities of the user. These alternative embodiments include those where substance is delivered in a separate gas flow, such as from a pressurized canister, for example, a pMDI canister.

In this embodiment the nosepiece 117 has a tapering section which narrows to the distal end thereof and acts, when inserted, typically from about 1 to 2 cm, into the anterior part of a nasal cavity, to expand the narrow nasal valve of the nasal cavity and provide a fluid-tight seal.

In this embodiment the mouthpiece 119 is configured to be gripped in the lips of a user. In an alternative embodiment the mouthpiece 119 could be configured to be gripped by the teeth of a user and sealed by the lips of the user. In a preferred embodiment the mouthpiece 119 is specifically configured to have one or both of a shape and geometry which allows the delivery device to be gripped repeatedly in the same position, thereby providing for the nosepiece 117 to be reliably inserted in the same position in the nasal cavity.

The delivery device further comprises a breath-actuated substance delivery assembly 124 for delivering substance through the main flow path 121 on exhalation by the user through the mouthpiece 119.

The substance supply assembly 124 comprises a substance supply unit 125 for delivering a metered dose of a substance on actuation of the same, an outlet unit 127 which is connected to the substance supply unit 125 for delivering substance through the main flow path 121, a loading mechanism 129 for loading the substance supply unit 125, and a release mechanism 131 for releasing the substance supply unit 125 from a loaded, non-actuated position to the actuated position on exhalation by the user through the mouthpiece 119.

In this embodiment the substance supply unit 125, as a mechanical pump, comprises a container 133 containing a volume of liquid containing a substance, a pump fitting 135 which includes a metering chamber and is connected to the container 133, and an outlet stem 137 which is movably disposed to the pump fitting 135 and through which liquid is delivered. In operation, a metered volume of liquid is delivered on relative movement of the pump fitting 135 and the outlet stem 137, in this embodiment movement of the pump fitting 135 in relation to the outlet stem 137, between a first position, as illustrated in FIG. 8(a), in which the outlet stem 137 is extended from the pump fitting 135 and a second position, as illustrated in FIG. 8(c), in which the outlet stem 137 is depressed into the pump fitting 135.

In this embodiment the substance supply unit 125 is a multi-dose device for enabling the delivery of a succession of metered doses of substance. In an alternative embodiment the substance supply unit 125 could be a single dose device for delivering a single metered dose of substance.

The pump fitting 135 includes at least one lug 138 which provides an abutment surface 139, as will be described in more detail hereinbelow. In this embodiment the abutment surface 139 of the at least one lug 138 is an inclined surface.

The outlet unit 127 comprises an outlet block 140 which is connected to the outlet stem 137 of the substance supply unit 125 and, in this embodiment, includes a valve and swirl chamber, and a delivery tube 141 from which a mist of fine droplets of the liquid is expelled on actuation of the substance supply unit 125. In an alternative embodiment the delivery tube 141 could be configured to deliver a liquid jet.

The loading mechanism 129 comprises a biasing element 143, in this embodiment a resilient element, here a compression spring, which is loaded with a predetermined force which is sufficient to actuate the substance supply unit 125 when released, in this embodiment by causing relative movement of the pump fitting 135 in relation to the outlet stem 137, and a loading member 145 for loading the biasing element 143. In this embodiment the loading member 145 comprises a lever which is movable to a loading position, as illustrated in FIG. 8(b), in which the loading member 145 acts to load the biasing element 143 by biasing the same against the bottom end of the container 133 of the substance supply unit 125.

The release mechanism 131 comprises a locking assembly 147 which acts to lock the substance supply unit 125 in the non-actuated position, in this embodiment by preventing movement of the pump fitting 135 relative to the outlet stem 137, until actuation of the release mechanism 131, and a trigger member 149 which is coupled to the locking assembly 147 and disposed at the mouthpiece 119 such as to support the locking assembly 147 until acted upon by an oral exhalation breath of a user.

In this embodiment the locking assembly 147 comprises a first, support member 151, which is hinged, in this embodiment to the outlet block 140 of the outlet unit 127, and engages the at least one lug 138 on the pump fitting 135 in the locked position, and a second, link member 153 which couples the support member 151 to the trigger member 149 when loaded.

In this embodiment the support member 151 is substantially L-shaped, with one end thereof being hinged to the outlet block 140 of the outlet unit 127, the other end thereof supporting the link member 153, and including an abutment surface 155, in this embodiment a curved surface, which engages the abutment surface 139 of the at least one lug 138 in the locked position. In this embodiment the link member 153 is hinged to the support member 151 such as to be freely movable between a first, locked position, as illustrated in FIG. 8(a), in which the link member 153 abuts the support member 151 and defines a support position, and a second, released position. In an alternative embodiment the link member 153 could comprise a flexible, preferably resilient, element.

In this embodiment the trigger member 149 comprises a pivot pin 157 about which the trigger member 149 is rotatable between a first, supporting position, as illustrated in FIG. 8(a), in which the trigger member 149 engages the locking assembly 147 in the locked position, and a second, released position, as illustrated in FIG. 8(c), in which the locking assembly 147 is not supported and released from the locking position.

In this embodiment the trigger member 149 further comprises a first, flow-sensitive vane 159 which extends from the pivot pin 157 and substantially closes the main flow path 121 when in the supporting position. In this embodiment the first vane 159 is configured to engage the abutment 123 in the main flow path 121 when in the supporting position. The provision of the abutment 123 acts to prevent the actuation of the substance supply unit 125 on inhalation by the user. In this embodiment the first vane 159 includes an aperture 160 which acts to require a predetermined air flow through the main flow path 121 prior to releasing the trigger member 149 from the supporting position. Advantageously, with this configuration, a bi-directional air flow can be achieved through the nasal cavities prior to release of substance through the nosepiece 117.

In this embodiment the trigger member 149 further comprises a second, pressure-sensitive vane 161 which extends from the pivot pin 157 and substantially seals the aperture 122 in the main flow path 121 when in the supporting position. In this embodiment the second vane 161 is configured such as to release the trigger member 149 from the supporting position on the generation of a predetermined pressure in the main flow path 121. Advantageously, with this configuration, the substance supply unit 125 can be actuated even when the nasal cavity is so congested that no, or not sufficient, an air flow can be achieved.

Operation of the delivery device will now be described hereinbelow.

In operation, a user first primes the device by rotating the loading member 145 of the loading mechanism 129 to the loaded configuration, as illustrated in FIG. 8(*b*). With the release mechanism 131 in the locked position, that is, with the abutment surface 155 of the supporting member 151 of the locking assembly 147 abutting the abutment surface 139 of the at least one lug 138 on the pump fitting 135, the biasing element 143 is biased against the bottom of the container 133 of the substance supply unit 125. The user then inserts the nosepiece 117 into one of the nasal cavities, grips the mouthpiece 119 with the lips, and exhales through the mouthpiece 119. Where an air flow can be established through the main flow path 121, by virtue of the aperture 160 in the first vane 159 of the trigger member 149, a bi-directional air flow is developed through the nasal cavities. With continued exhalation, the pressure differential across the first vane 159 of the trigger member 149 increases, until such point that the pressure differential is such as to cause the rotation of the first vane 159 and thereby the pivot pin 157 to which the first vane 159 is attached. Where an air flow cannot be established, for example, as a result of nasal congestion, the pressure in the main flow path 121 increases, until such point that the pressure acts to cause the rotation of the second vane 161 and thereby the pivot pin 157 to which the second vane 161 is attached. This rotation of the pivot pin 157 is such as to cause the movement of the link member 153 of the locking assembly 147, which link member 153, once no longer abutting the pivot pin 157 and supporting the locking assembly 147 in the locking configuration, allows for the movement, under the action of the biasing element 143, of the container 133 and the pump fitting 135 coupled thereto to actuate the substance supply unit 125 and deliver a metered volume of liquid from the delivery tube 141 of the outlet unit 127.

Figure 10A:
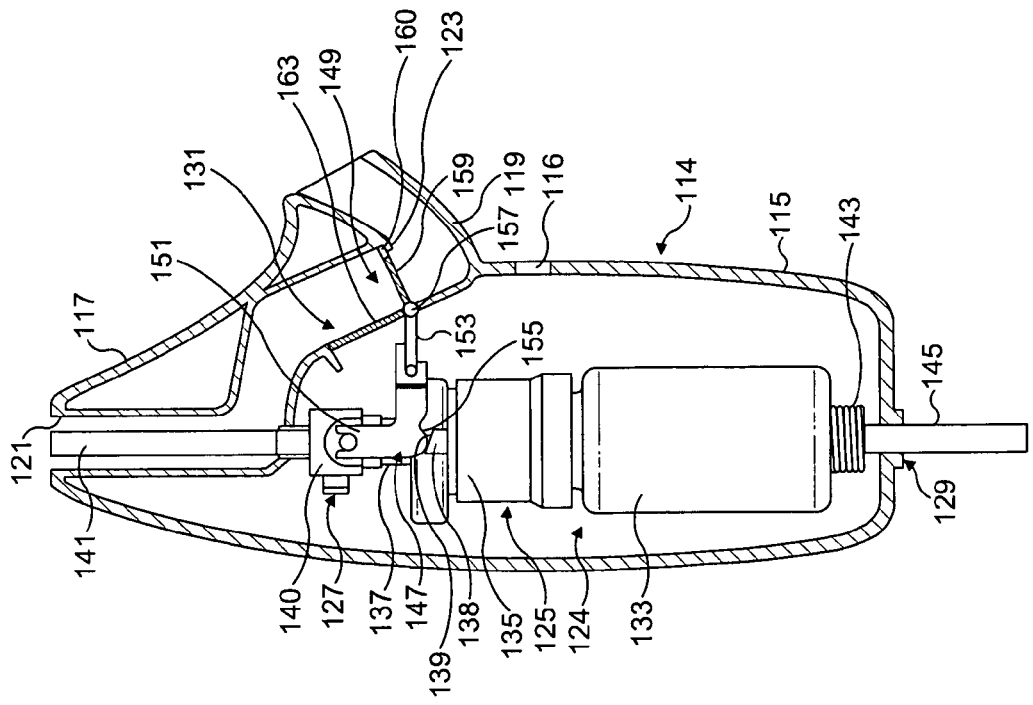
FIG. 10(a) illustrates a part-sectional view of a nasal delivery device in accordance with a third embodiment of the present invention, illustrated in an inoperative, rest configuration.
Figure 10B:
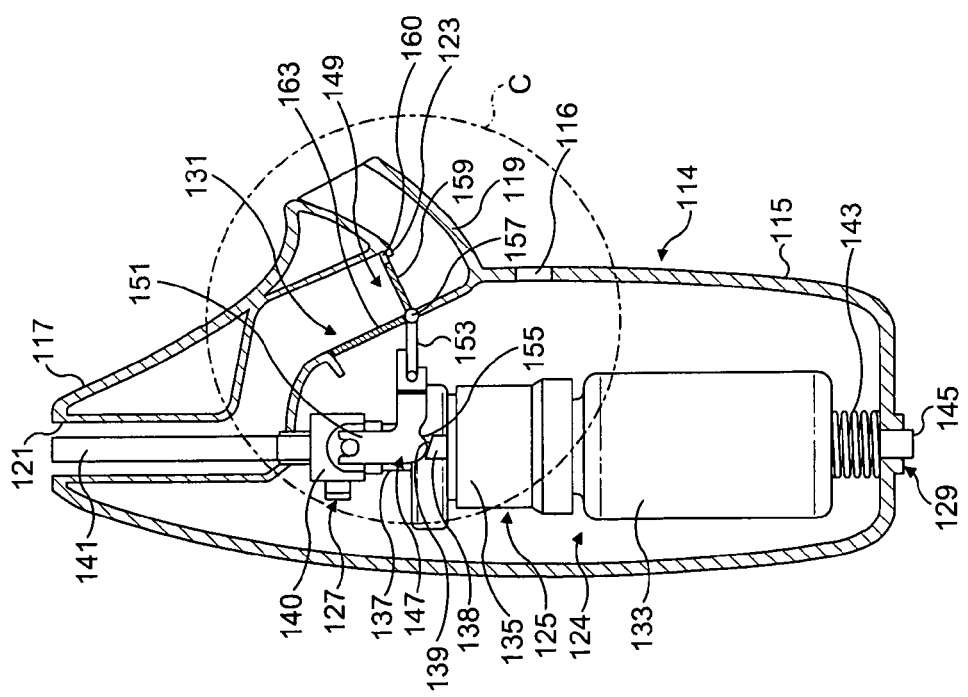
FIG. 10(b) illustrates a part-sectional view of the nasal delivery device of FIG. 10(a) in a loaded, operable configuration.
Figure 10C:
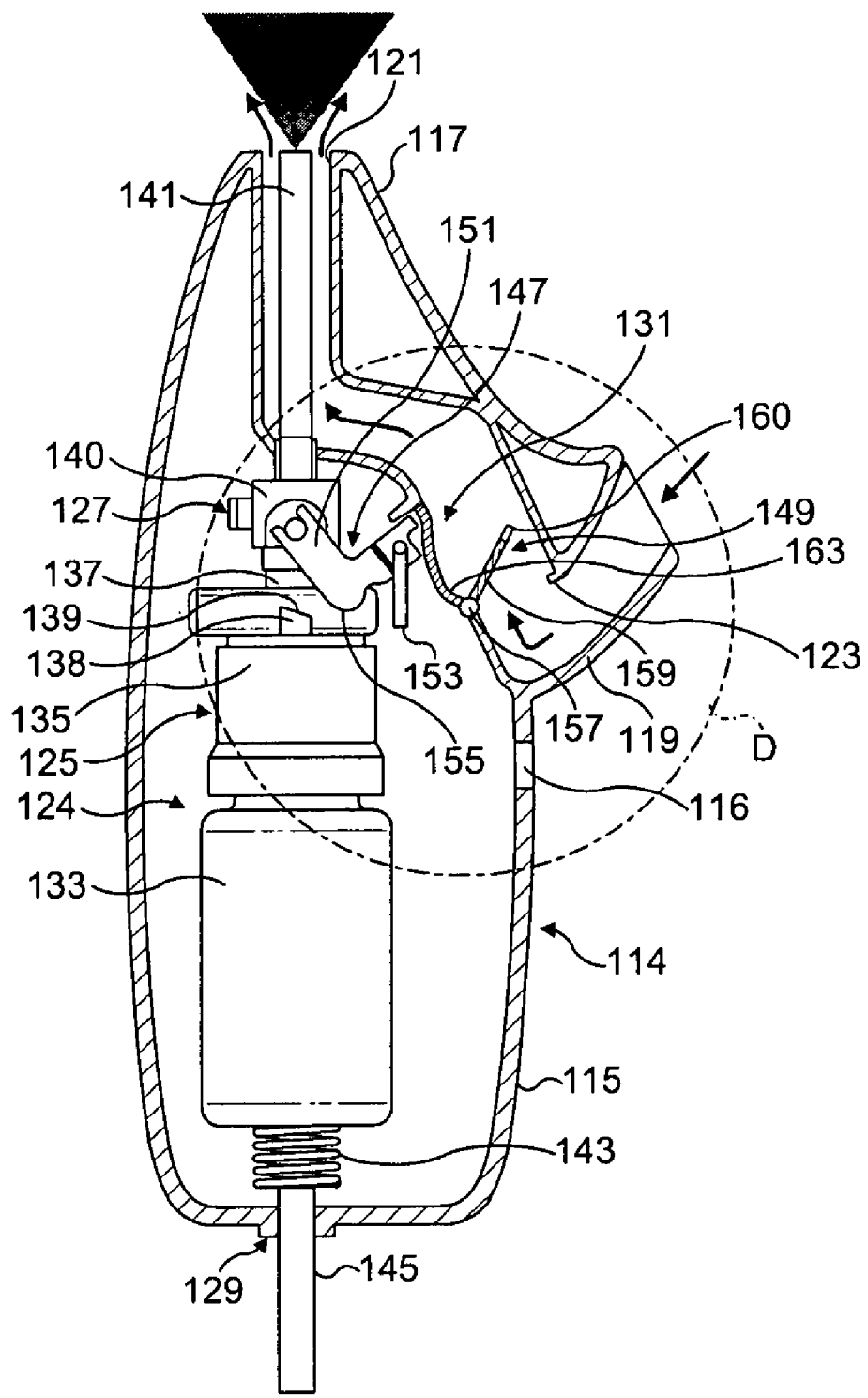
FIG. 10(c) illustrates a part-sectional view of the nasal delivery device of FIG. 10(a) in an actuated configuration.
Figure 11A:
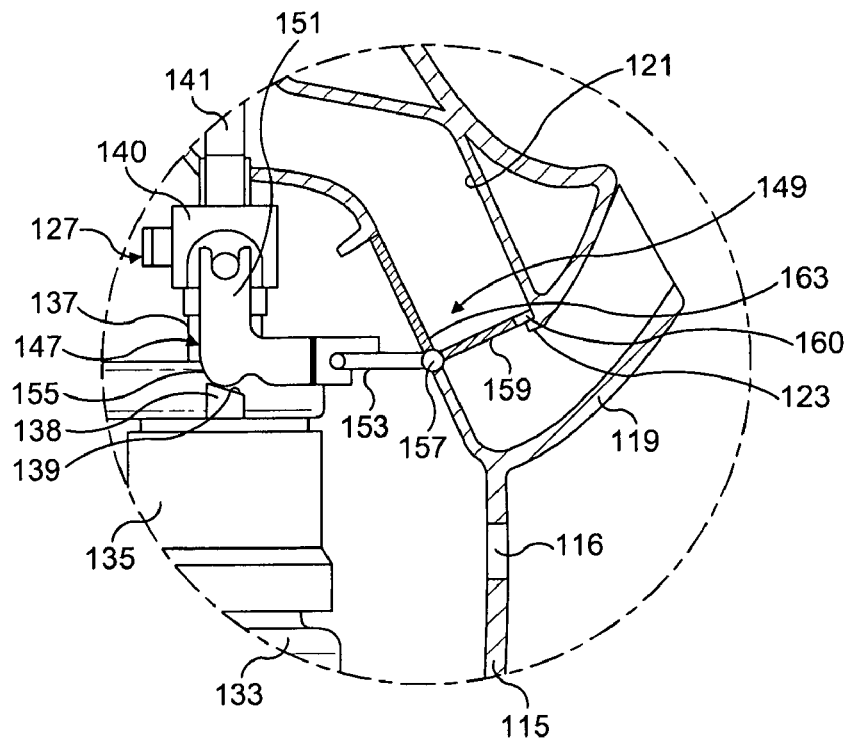
FIG. 11(a) illustrates in enlarged scale region C of FIG. 10(a)
Figure 11B:
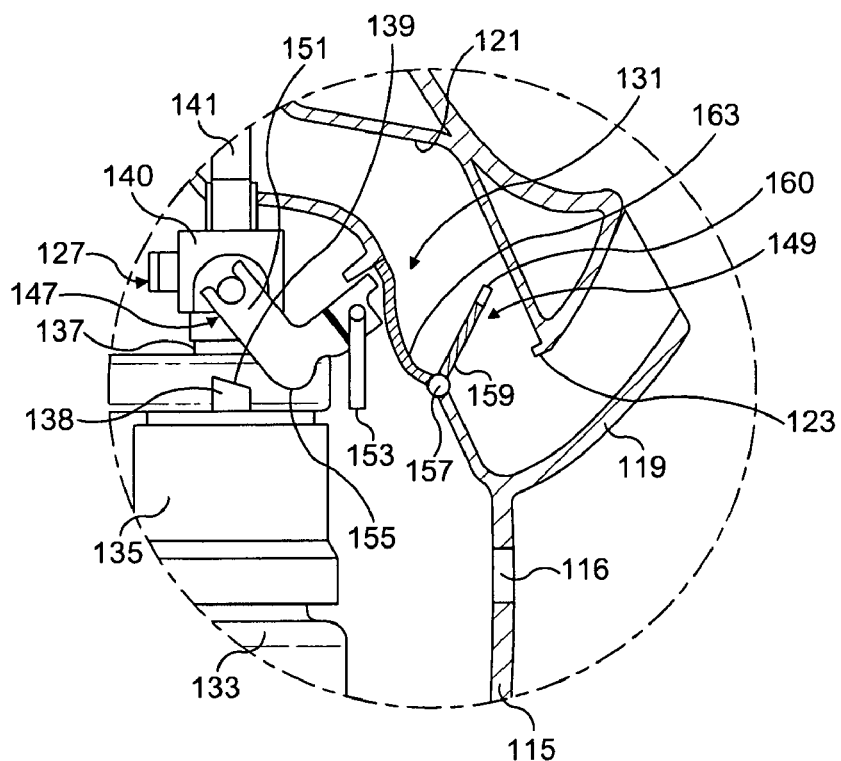
FIG. 11(b) illustrates in enlarged scale region D of FIG. 10(c)

FIGS. 10 and 11 illustrate a breath-actuated nasal delivery device in accordance with a third embodiment of the present invention.

The nasal delivery device of this embodiment is very similar to that of the above-described second embodiment. Thus, in order to avoid unnecessary duplication of description, only the differences will be described in detail, with like parts being designated by like reference signs.

The nasal delivery device of this embodiment differs only in that the trigger member 149 does not include a second vane 161 as in the above-described second embodiment, but instead comprises a resilient element 163 which acts as a pressure-sensitive element. Operation is the same as for the above-described embodiment, with the resilient element 163 being deformed, and hence causing rotation of the pivot pin 157, with an increased pressure in the main flow path 121, such that the pivot pin 157 is rotated sufficiently to release the locking assembly 147 on a predetermined pressure being developed in the main flow path 121.

In alternative embodiments the trigger member 149 could be configured to include only a single vane 159, 161 or element 163 such that the trigger member 149 is only one of flow or pressure sensitive. In particular, where the exhalation breath of a user is not delivered to the nasal airway, that is, where the nosepiece 117 is not fluidly connected to the mouthpiece 119, the trigger member 149 need only be configured to be one of flow or pressure sensitive, since there will be no obstruction to the exhalation breath.

For example, in these embodiments the substance supply unit 125 could comprise an aerosol canister, such as used in a pressurized metered dose inhaler (pMDI), for delivering a propellant, preferably a hydrofluoroalkane (HFA) propellant or the like, containing a substance, preferably a medicament either as a suspension or a solution.

In other embodiments the substance supply unit 125 could comprise a dry powder delivery unit for delivering a metered dose of substance in a dry powder, either entrained in the exhalation breath of a user or in a separate gas flow as supplied by a separate gas source.

In still yet other embodiments the substance supply unit 125 could comprise a nebulizer for delivering a metered dose of a nebulized substance, either entrained in the exhalation breath of a user or in a separate gas flow as supplied by a separate gas source.

In still yet also other embodiments the substance supply unit 125 could comprise a jet pump which delivers, in this embodiment squirts, a metered dose of a substance as a jet on actuation thereof, typically by releasing the stored energy in a compression spring.

In these embodiments the delivery device is configured to deliver the exhalation breath through one nostril of a user such as to flow around the posterior margin of the nasal septum and out of the other nostril of the user, thereby achieving bi-directional flow through the nasal cavities as disclosed in WO-A-00/51672.

In alternative embodiments the delivery device could be configured to deliver substance at a reduced pressure which is not sufficient to achieve bi-directional delivery through the nasal cavities. This notwithstanding, these embodiments are still advantageous as compared to known delivery devices in providing for velum closure and being capable of achieving targeted delivery. In one embodiment the delivery device could include two nosepieces 117 for the simultaneous delivery to each of the nasal cavities. This embodiment advantageously provides for three-point fixation of the delivery device via the nosepieces 117 and the mouthpiece 119.

Figure 12A:
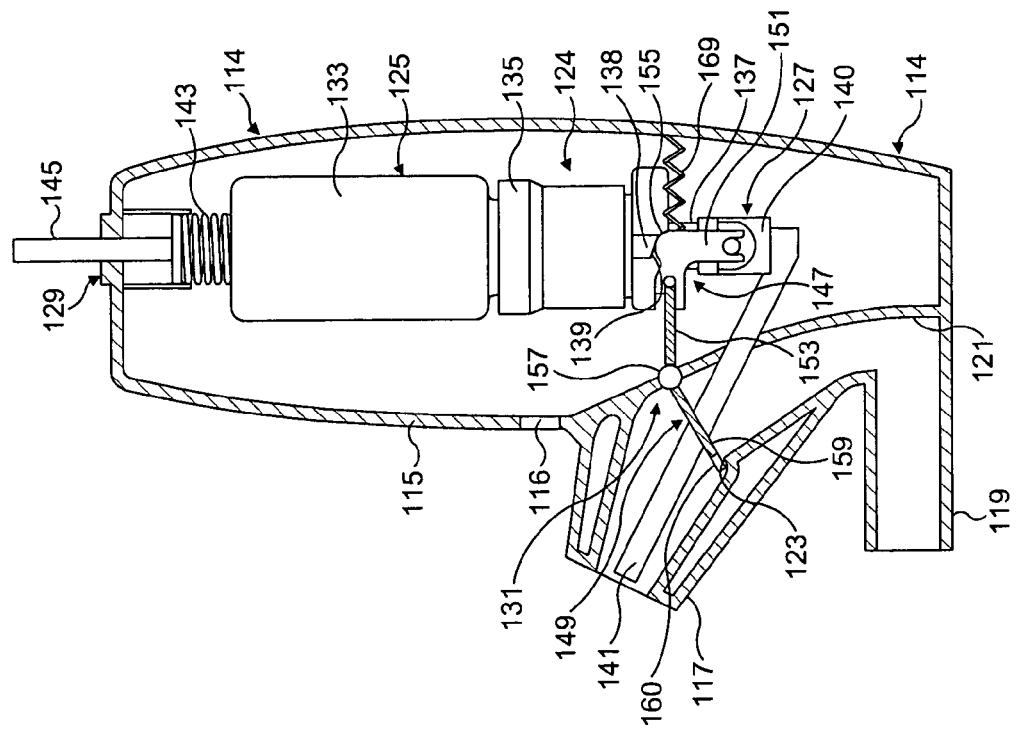
FIG. 12(a) illustrates a part-sectional view of a nasal delivery device in accordance with a fourth embodiment of the present invention, illustrated in an inoperative, rest configuration.
Figure 12B:
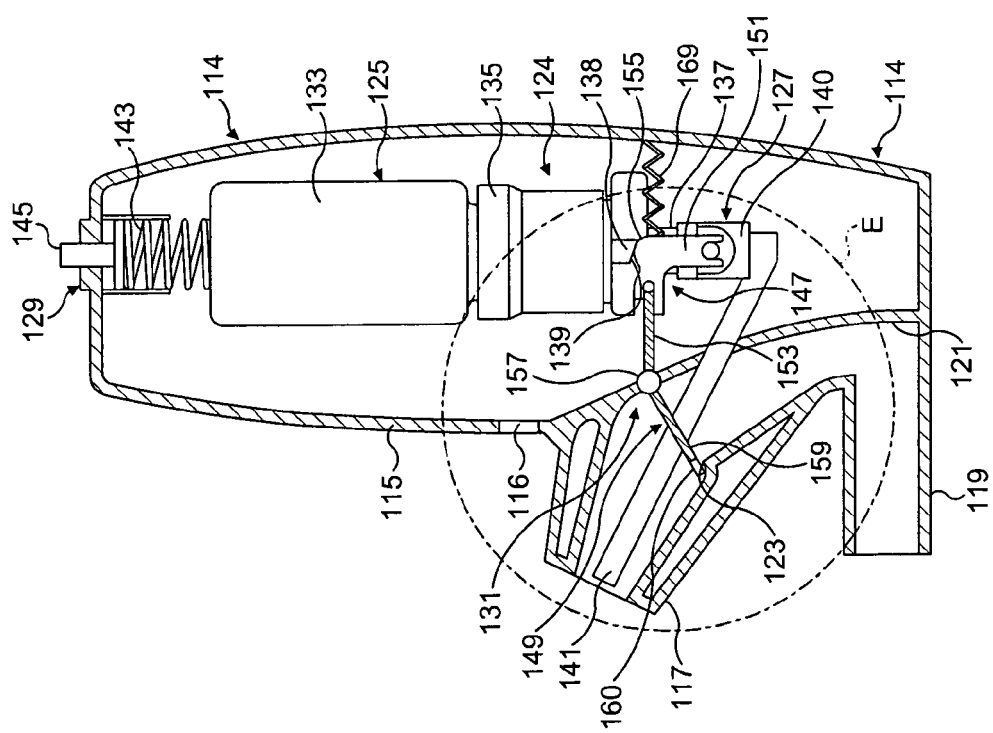
FIG. 12(b) illustrates a part-sectional view of the nasal delivery device of FIG. 12(a) in a loaded, operable configuration.
Figure 12C:
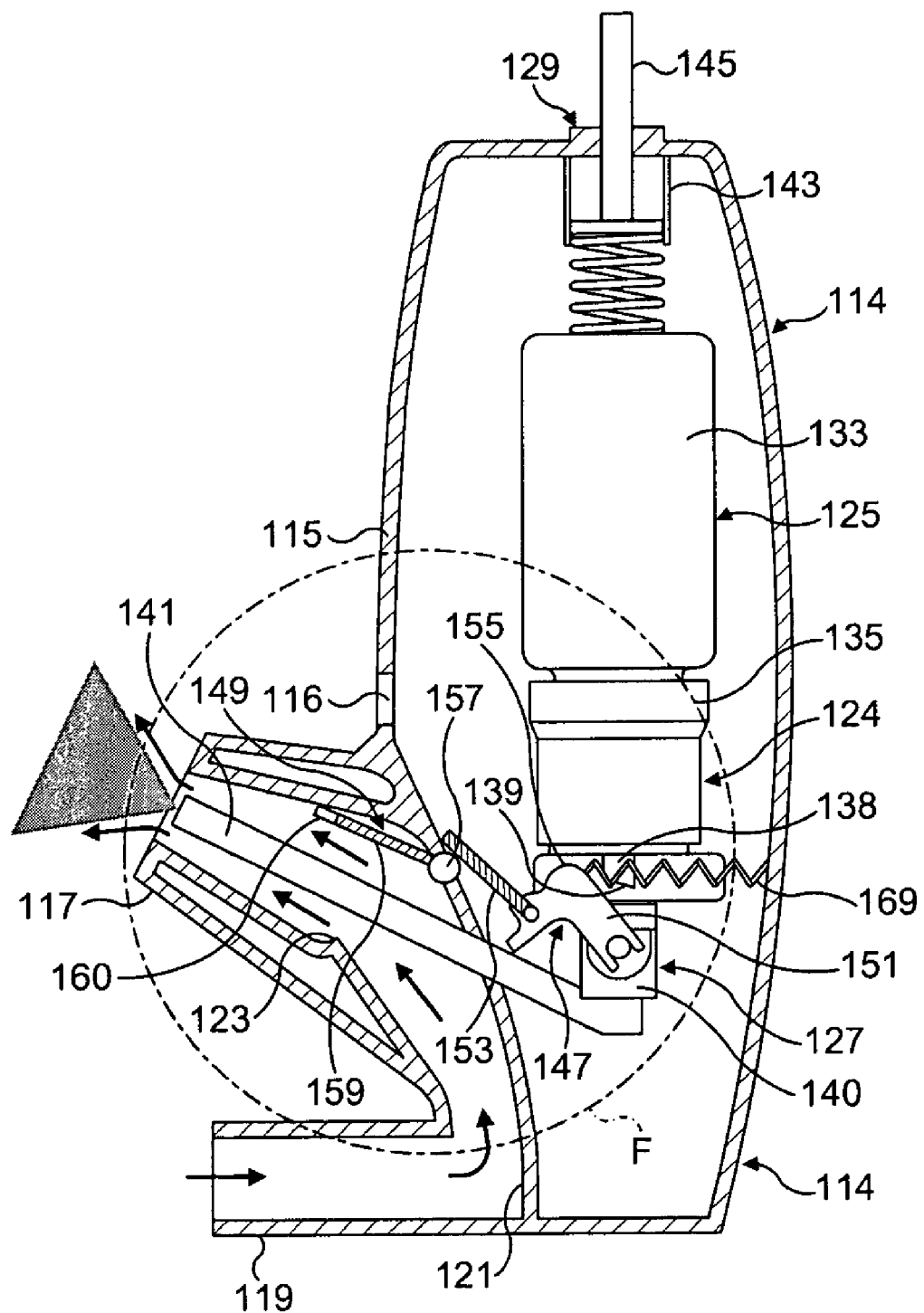
FIG. 12(c) illustrates a part-sectional view of the nasal delivery device of FIG. 12(a) in an actuated configuration.
Figure 13A:
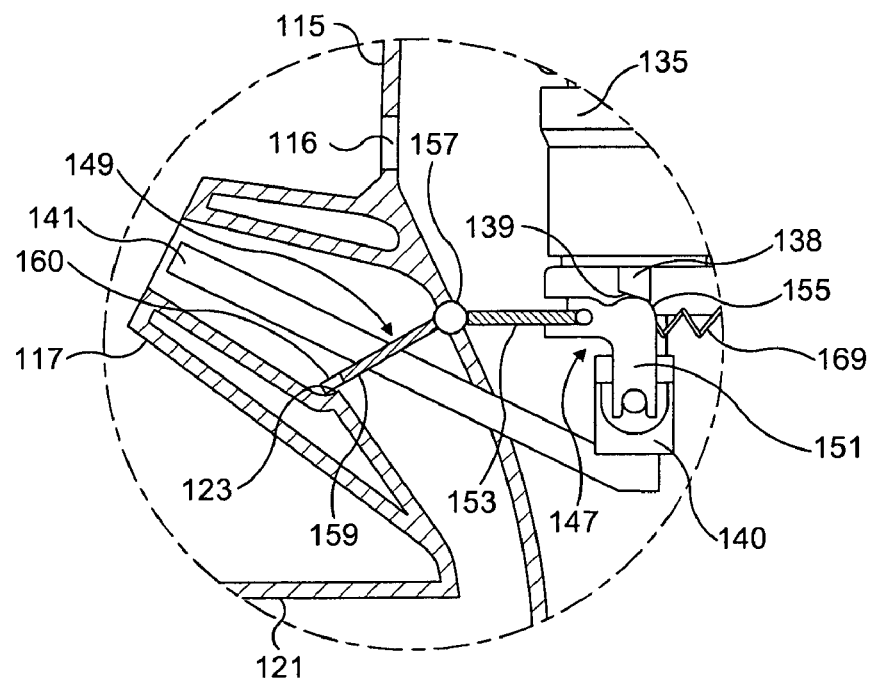
FIG. 13(a) illustrates in enlarged scale region E of FIG. 12(a)
Figure 13B:
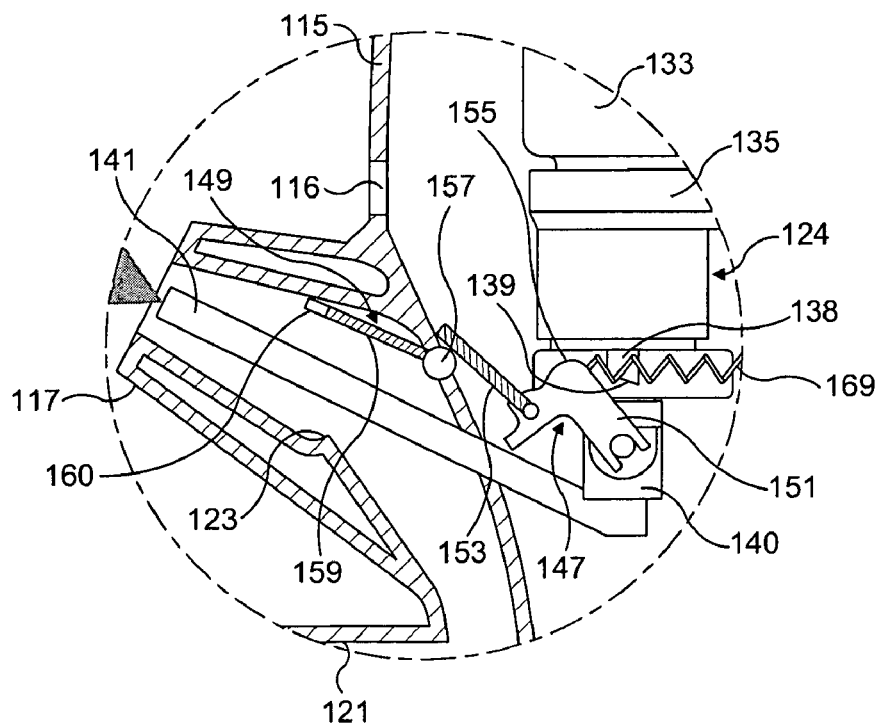
FIG. 13(b) illustrates in enlarged scale region F of FIG. 12(c)

FIGS. 12 and 13 illustrate a breath-actuated nasal delivery device in accordance with a fourth embodiment of the present invention.

The nasal delivery device of this embodiment is very similar to that of the above-described second and third embodiments. Thus, in order to avoid unnecessary duplication of description, only the differences will be described in detail, with like parts being designated by like reference signs.

The nasal delivery device of this embodiment differs principally only in that the substance supply unit 125 is an aerosol canister, such as used in a pressurized metered dose inhaler (pMDI), for delivering a propellant, preferably a hydrofluoroalkane (HFA) propellant or the like, containing a substance, in that the release mechanism 131 further comprises a biasing element 169, in this embodiment a resilient element, for biasing the locking assembly 147 to the locking configuration, and in that the trigger member 149 comprises only a single flow-sensitive vane 159. In a preferred embodiment the aerosol canister is a pressurized metered dose inhaler (pMDI), for delivering a propellant, preferably a hydrofluoroalkane (HFA) propellant or the like, containing a substance, preferably a medicament either as a suspension or a solution. Operation is the same as for the above-described second and third embodiments.

FIGS. 14 and 15 illustrate a flow-control mechanism in accordance with an embodiment of the present invention for incorporation in the main flow path 21, 121 between the mouthpiece 19, 119 and the trigger member 61, 149 of the nasal delivery devices of the above-described embodiments.

Where a spray pump is operated in an inclined orient, typically more than 45 degrees, or an upside-down orient, air may be drawn into the pump fitting, causing at least in part air, and not liquid, to be pumped. This will have the effect of causing a sequence of subsequent doses to be incomplete, and the flow-control mechanism is configured thus to prevent a user from releasing the device in an incorrect orient.

Figure 14B:
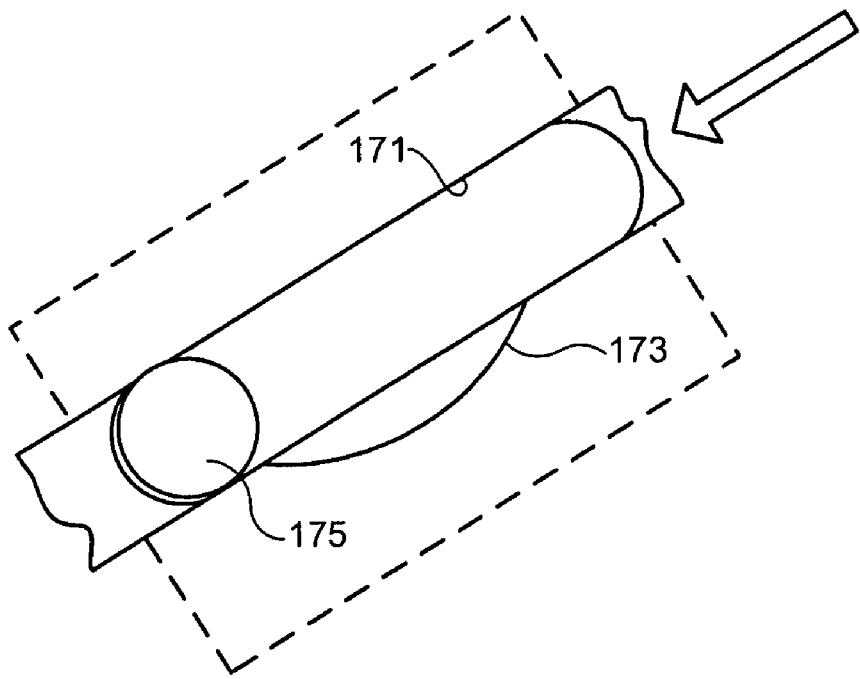

In this embodiment, as illustrated in FIG. 14(a), the flow-control mechanism comprises a flow channel section 171 which includes a recess 173, and a ball 175 which is movably captively disposed within the flow channel section 171 and normally, with the delivery device in an acceptable orient, rests in the recess 173 to allow an air flow from the mouthpiece 19, 119 to the trigger member 61, 149, but, with the delivery device in an unacceptable orient, the ball 175 adopts a forward, downstream position in the flow channel section 171 to block the same and prevent the development of an air flow therethrough which is required to actuate the release mechanism 34, 131. A user is most likely to attempt to operate the device when seated with their head tilted backwards or in the supine position. Where the device is tilted backwards more than a predetermined angle, as illustrated in FIG. 14(b), the ball 175 will roll from the recess 173 into a narrower, downstream part of the flow channel section 171 and block the same, thereby preventing actuation of the release mechanism 34, 131. A more complex mechanism may also prevent insufflations in this position.

In this embodiment the flow-control mechanism is also configured to prevent actuation of the release mechanism 34, 131 where a user blows too forcefully into the device. It can be advantageous to first establish a certain flow through the device and into the nose before releasing substance. The shape and/or geometry of the flow channel section 171 at the recess 173 allows for the passage of a certain air flow, as illustrated in FIG. 15(a), but, if the air flow becomes too high, the ball 175 is blown into the narrow, downstream region of the flow channel section 175, as illustrated in FIG. 15(b), blocking off the flow channel section 171, and hence the main flow path 21, 121, and thereby preventing air flow through the main flow path 21, 121, and consequently actuation of the device. The shape and geometry of the recess 173, the angling of the flow channel section 171 at the end regions thereof and the weight of the ball 175 can be altered to determine the maximum permitted flow.

Also, in this embodiment, where inhalation is attempted, the ball 175 will be sucked into the narrow, upstream region of the flow channel section 171, preventing further air flow, as illustrated in FIG. 15(c).

Finally, it will be understood that the present invention has been described in its preferred embodiments and can be modified in many different ways without departing from the scope of the invention as defined in the appended claims.

For example, for mechanical spray pumps, issues related to priming and loss of priming are important. Normally, when the container 35, 133 is new, the pump must be compressed typically three to five times before providing the first mist at actuation. In order to ensure that the required priming is performed before the device is used, in one modification a counter is included which clearly shows that the device is primed. The subject should be able to see that the device actually fires before it is used.

In another modification the device is configured to provide for manual firing, especially in the case where a conventional container 35, 133 is used which may suck air into the tube and chamber if the container 35, 133 is held in an incorrect orient. With the traditional spray pumps, the dose in the chamber tends to evaporate after some hours or days, making it necessary to re-prime the pump to enable proper function where having not been used for a certain period. However, recently, a new pump design has been developed which incorporates a valve, preventing this loss of prime. Still, the problem of actuating in an upside-down or very-tilted position remains. If actuated in this position, air may be drawn into the tube inside the container 35, 133 instead of liquid. This causes one or more of the subsequent doses to be incomplete. This may require repeated re-priming to restore normal function. One solution is to provide a compliant membrane inside the container 35, 133 to prevent air entering the tube. Still, this solution is more expensive and the flexible membrane inside the container 35, 133 is formed other than from glass. To change from glass may be costly, and may hinder the uptake of this solution, particularly where used for medicaments. The present mechanism, which prevents release in upside-down and very-tilted orients, will to a large extent obviate this problem.

In the described embodiments the hinge axis of the support member 63, 151 of the locking assembly 59, 147 is co-incident with the axis of the substance supply unit 31, 125, but the hinge axis of the support member 63, 151 could be offset from the axis of the substance supply unit 31, 125.

The invention claimed is:

1. A breath-actuated nasal delivery device, comprising:
   a mouthpiece through which a user in use exhales to actuate the delivery device;
   a nosepiece for fitting to a nostril of the user through which a substance is in use delivered;
   a substance supply unit actuatable to deliver a dose of a substance through the nosepiece;
   a loading unit operable to load the substance supply unit with an actuation force; and
   a release mechanism for enabling actuation of the substance supply unit in response to exhalation by the user through the mouthpiece; wherein the release mechanism comprises a locking unit which is movable between a locking configuration in which the substance supply unit is locked in a non-actuated position when loaded by the loading unit and a release configuration in which the substance supply unit is actuatable by the loading unit, and a trigger member for releasing the locking unit from the locking configuration to the release configuration in response to exhalation by the user through the mouthpiece and thereby enabling actuation of the substance supply unit.

2. The delivery device of claim 1, wherein the trigger member comprises a flow-sensitive element in fluid communication with the mouthpiece.

3. The delivery device of claim 2, wherein the flow-sensitive element comprises a vane.

4. The delivery device of claim 2, wherein the flow-sensitive element includes an aperture which allows for a predetermined air flow thereover prior to actuation.

5. The delivery device of claim 2, wherein the flow-sensitive element is one or both of shaped and sized such as to allow for a predetermined air flow thereover prior to actuation.

6. The delivery device of claim 1, wherein the trigger member comprises a pressure-sensitive element in fluid communication with the mouthpiece.

7. The delivery device of claim 6, wherein the pressure-sensitive element comprises a vane.

8. The delivery device of claim 6, wherein the pressure-sensitive element comprises a flexible membrane.

9. The delivery device of claim 8, wherein the flexible membrane comprises a resilient membrane.

10. The delivery device of claim 6, wherein the pressure-sensitive element comprises a flexible membrane in fluid communication with the mouthpiece and a vane operable by the flexible membrane.

11. The delivery device of claim 10, wherein the flexible membrane comprises a resilient membrane.

12. The delivery device of claim 1, further comprising:
a pressure-sensitive sealing unit disposed downstream of the trigger member and being operable to vent air flow developed by the user on exhalation through the mouthpiece to atmosphere, the sealing unit being normally closed and operable such as to be opened on generation of a predetermined pressure thereat.

13. The delivery device of claim 12, wherein the sealing unit comprises an annular seal, a sealing member movable between a closed position in sealing engagement with the annular seal and an open position in which an air flow can flow through the annular seal, and a biasing element for normally biasing the sealing member to the closed position and enabling the sealing member to be opened on generation of a predetermined pressure thereat.

14. The delivery device of claim 12, wherein the sealing unit comprises a flexible membrane which is movable between a closed position and an open position in which an air flow can flow thereby.

15. The delivery device of claim 14, wherein the flexible membrane comprises a resilient membrane.

16. The delivery device of claim 1, wherein the trigger member includes a pivot pin about which the same is rotatable, which pivot pin is engaged by the locking unit when in the locking configuration such that the locking unit is moved from the locking configuration to the release configuration on rotation of the pivot pin.

17. The delivery device of claim 16, wherein the locking unit includes a first, support member which abuts the substance supply unit in the locking configuration and a second, link member which engages the pivot pin of the trigger member in the locking configuration, wherein the link member is movable in relation to the support member and configured to be moved on rotation of the pivot pin to move the locking unit from the locking configuration to the release configuration.

18. The delivery device of claim 17, wherein the link member is rotatably connected to the support member.

19. The delivery device of claim 17, wherein the link member is configured to load the pivot pin radially.

20. The delivery device of claim 1, further comprising:
a flow path fluidly connecting the nosepiece and the mouthpiece, whereby an air flow developed by exhalation by the user through the mouthpiece is delivered through the nosepiece.

21. The delivery device of claim 1, wherein the nosepiece and the mouthpiece are fluidly isolated.

22. The delivery device of claim 1, wherein the substance supply unit comprises a nebulizer for supplying an aerosol.

23. The delivery device of claim 1, wherein the substance supply unit comprises an aerosol canister for supplying an aerosol.

24. The delivery device of claim 1, wherein the substance supply unit comprises a delivery pump unit for supplying one of an aerosol or a jet.

25. The delivery device of claim 24, wherein the delivery pump unit comprises a liquid pump unit for supplying a liquid aerosol.

26. The delivery device of claim 24, wherein the delivery pump unit comprises a powder pump unit for supplying a powder aerosol.

27. The delivery device of claim 1, wherein the substance supply unit comprises a powder delivery unit for delivering a powder aerosol.

28. The delivery device of claim 1, further comprising:
a flow-control mechanism disposed upstream of the trigger member to at least restrict an air flow to the trigger member such as to prevent actuation of the release mechanism on exhalation by the user through the mouthpiece where the delivery device is being improperly operated.

29. The delivery device of claim 28, wherein the flow-control mechanism is configured to at least restrict the air flow to the trigger member where the delivery device is in an improper orient.

30. The delivery device of claim 28, wherein the flow-control mechanism is configured to at least restrict the air flow to the trigger member where the air flow developed by the user has a rate exceeding a predetermined threshold value.

31. The delivery device of claim 28, wherein the flow control mechanism comprises a flow channel section which includes a recess, and a ball which is movably, captively disposed within the flow channel section, the ball normally, with proper operation of the delivery device, resting in the recess such as to allow a sufficient air flow to the trigger member as to enable actuation of the release mechanism, and being moved to at least partially block the flow channel section where the delivery device is being improperly operated such as to prevent actuation of the release mechanism.

32. A breath-actuated nasal delivery device, comprising:
a mouthpiece through which a user in use exhales to actuate the delivery device;
a nosepiece for fitting to a nostril of the user through which a substance is in use delivered and being in fluid communication with the mouthpiece;
a substance supply unit actuatable to deliver a dose of a substance through the nosepiece;
a release mechanism for enabling actuation of the substance supply unit in response to exhalation by the user through the mouthpiece; and
a flow-control mechanism disposed upstream of a trigger member to at least restrict an air flow to the trigger member such as to prevent actuation of the release mechanism on exhalation by the user through the mouthpiece where the delivery device is being improperly operated.

33. The delivery device of claim 32, wherein the flow-control mechanism is configured to at least restrict the air flow to the trigger member where the delivery device is in an improper orient.

34. The delivery device of claim 32, wherein the flow-control mechanism is configured to at least restrict the air flow to the trigger member where the air flow developed by the user has a rate exceeding a predetermined threshold value.

35. The delivery device of claim 32, wherein the flow-control mechanism comprises a flow channel section which includes a recess, and a ball which is movably, captively disposed within the flow channel section, the ball normally, with proper operation of the delivery device, resting in the recess such as to allow a sufficient air flow to the trigger member as to enable actuation of the release mechanism, and being moved to at least partially block the flow channel section where the delivery device is being improperly operated such as to prevent actuation of the release mechanism.

36. A release mechanism for enabling actuation of a substance supply unit, the release mechanism comprising:
a locking unit which is movable between a locking configuration in which the substance supply unit is locked in a non-actuated position and a release configuration in which the substance supply unit is actuatable; and a trigger member for releasing the locking unit from the locking configuration to the release configuration in response to a gas flow thereat, wherein the gas flow is developed by a user's exhalation, and wherein the trigger member includes a pivot pin about which the same is rotatable, which pivot pin is engaged by the locking unit when in the locking configuration such that the locking unit is moved from the locking configuration to the release configuration on rotation of the pivot pin.

37. The release mechanism of claim 36, where in the locking unit includes a first, support member which abuts the substance supply unit in the locking configuration and a second, link member which engages the pivot pin of the trigger member in the locking configuration, wherein the link member is movable in relation to the support member and configured to be moved on rotation of the pivot pin to move the locking unit from the locking configuration to the release configuration.

38. The release mechanism of claim 37, wherein the link member is rotatably connected to the support member.

39. The release mechanism of claim 37, wherein the link member is configured to load the pivot pin radially.

* * * * *